US007341859B2

(12) United States Patent
Hummel et al.

(10) Patent No.: US 7,341,859 B2
(45) Date of Patent: Mar. 11, 2008

(54) **ADH FROM *RHODOCOCCUS ERYTHROPOLIS***

(75) Inventors: Werner Hummel, Titz (DE); Kofi Abokitse, Aachen (DE); Harald Groeger, Hanau (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/508,702

(22) PCT Filed: Apr. 1, 2003

(86) PCT No.: PCT/EP03/03375

§ 371 (c)(1),
(2), (4) Date: Jul. 11, 2005

(87) PCT Pub. No.: WO03/091423

PCT Pub. Date: Nov. 6, 2003

(65) Prior Publication Data

US 2006/0246561 A1    Nov. 2, 2006

(30) Foreign Application Priority Data

Apr. 26, 2002  (DE)  ................. 102 18 689

(51) Int. Cl.
*C12N 1/20* (2006.01)
*C12N 9/02* (2006.01)
*C12N 15/74* (2006.01)
*C12P 21/06* (2006.01)
*C12Q 1/68* (2006.01)
*G01N 33/567* (2006.01)
*C07H 21/06* (2006.01)

(52) U.S. Cl. .................. 435/252.3; 435/6; 435/7.2; 435/69.1; 435/471; 435/189; 435/155; 536/23.2

(58) Field of Classification Search ............. 435/252.3, 435/471, 155, 189; 536/23.2
See application file for complete search history.

(56) References Cited

U.S. PATENT DOCUMENTS

| 2003/0100065 A1 | 5/2003 | Hummel et al. |
| 2003/0224279 A1 | 12/2003 | Kotsugai et al. |
| 2005/0064570 A1 | 3/2005 | Hummel et al. |
| 2006/0216801 A1 | 9/2006 | Groger et al. |
| 2006/0246561 A1 | 11/2006 | Hummel et al. |
| 2007/0149781 A1 | 6/2007 | Riermeier et al. |

FOREIGN PATENT DOCUMENTS

| DE | 42 09 022 | 10/1993 |
| EP | 1 201 647 | 5/2002 |
| EP | 1 213 354 | 6/2002 |

OTHER PUBLICATIONS

Hummel et al. Towards a Large-Scale Asymmetric Reduction Process with Isolated Enzymes: Expression of an (S)-Alcohol Dehydrogenase in *E. coli* and Studies on the Synthetic Potential of this Biocatalyst, Adv. Synth. Catal. 345, Jan. 21, 2003.*

Wang, J.-C. et al. "Cloning, sequence analysis and expression in *Escherichia coli* of the gene encoding phenylacetaldehyde reductase from styrene-assimilating Corynebacterium sp. Strain ST-10", Appl. Microbiol. Biotechnol., vol. 52, No. 3, pp. 386-392, XP002221908 1999.

Itoh, Nobuya et al. "Purification and Characterization of Phenylacetaldehyde Reductase from a Styrene- Assimilating Corynebacterium Strain, ST-10", Applied and Environmental Microbiology, vol. 63, No. 10, pp. 3783-3788, XP002221910 1997.

Itoh, Nobuya et al. "Production of Chiral Alcohols by Enantioselective Reduction with NADH-dependent phenylacetaldehyde reductase from Corynebacterium strain, ST-10", Journal of Molecular Catalysis B: Enzymatic, vol. 6, No. 1-2, pp. 41-50, XP002221909 1999.

Hummel, Werner. "New Alcohol Dehydrogenases for the Synthesis of Chiral Compounds", Advances in Biochemical Engineering/ Biotechnology, vol. 58, pp. 145-184, XP000677754 1997.

Schenkels, Peter et al. "Nicotinoprotein (NADH-containing) alcohol dehydrogenase from *Rhodococcus erythropolis* DSM 1069: an efficient catalyst for coenzyme-independent oxidation of a broad spectrum of alcohols and the interconversion of alcohols and aldehydes", Microbiology, vol. 146, No. 4, pp. 775-785, XP002253322 2000.

Reid, Matthew F. et al. "Molecular Characterization of Microbial Alcohol Dehydrogenases", Critical Reviews in Microbiology, vol. 20, No. 1, pp. 13-56, XP002110760 1994.

Hummel, W. et al., "Chiral Alcohols by Enantioselective Enzymatic Oxidation", Annals New York Academy of Sciences, vol. 799, pp. 713-716, XP000677513 1996.

U.S. Appl. No. 11/766,164, filed Jun. 21, 2007, Groeger et al.
U.S. Appl. No. 11/766,189, filed Jun. 21, 2007, Groeger et al.
U.S. Appl. No. 11/736,351, filed Apr. 17, 2007, Yamaguchi et al.
U.S. Appl. No. 11/629,407, filed Dec. 13, 2006, Groeger et al.
U.S. Appl. No. 10/521,445, filed Jan. 14, 2005, Groeger et al.
U.S. Appl. No. 10/521,456, filed Jan. 18, 2005, Groeger et al.
U.S. Appl. No. 10/508,702, filed Sep. 29, 2004, Hummel et al.
U.S. Appl. No. 10/546,733, filed Aug. 24, 2005, Rollmann et al.
U.S. Appl. No. 10/492,939, filed Apr. 19, 2004, May et al.
U.S. Appl. No. 10/508,702, filed Jul. 11, 2005, Hummel et al.
U.S. Appl. No. 10/593,567, filed Sep. 20, 2006, Groeger et al.

* cited by examiner

*Primary Examiner*—Rebecca E. Prouty
*Assistant Examiner*—Iqbal Chowdhury
(74) *Attorney, Agent, or Firm*—Oblon, Spivak, McClelland, Maier & Neustadt, P.C.

(57) ABSTRACT

The present invention relates to an alcohol dehydrogenase from *Rhodococcus erythropolis*. By means of such cofactor-dependent ADHs, chiral alcohols, which can be of use for use in organic syntheses, can advantageously be obtained with a cofactor-regenerating enzyme in a coupled enzymatic system. A nucleotide sequence, vehicles containing this, a polypeptide sequence and processes for mutation and use of the sequences are claimed.

3 Claims, 5 Drawing Sheets

Figure 1:
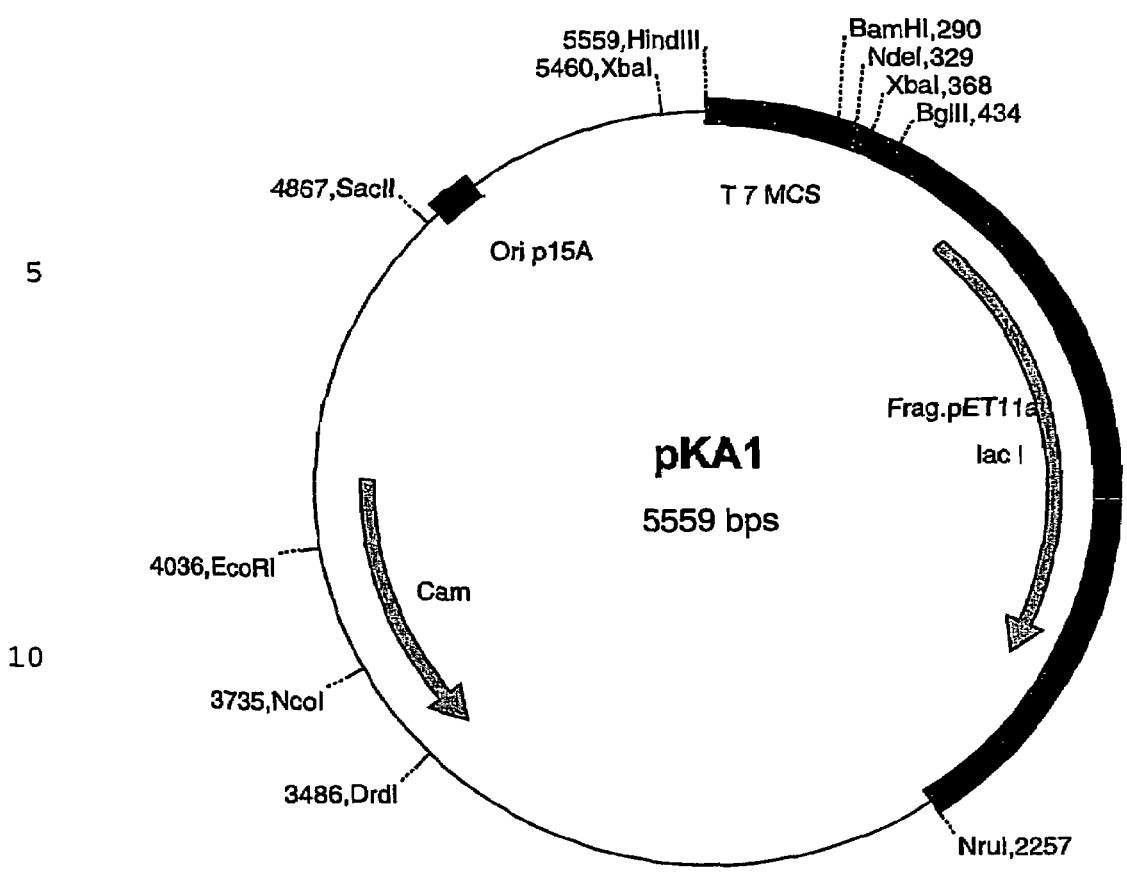

Fig. 3:

```
READH:  1
atgaaggcaatccagtacacgagaatcggcgcggaacccgaactcacggagattcccaaa 60
        |||||| ||||||||||||||
||||||||||||            ||||||||||||||||||||
Coryn:  1
atgaaggcgatccagtacacgcgaatcggcgcggaacccgaactcacggagattcccaaa 60

READH:  61
cccgagcccggtccaggtgaagtgctcctggaagtcaccgctgccggcgtctgccactcg 120
                   ||||||||||||||||||||||||||||| |||||||||||||
||||||||||||||
Coryn:  61
cccgagcccggtccaggtgaagtgctcctggaagtcaccgctgctggcgtctgccactcg 120

READH:  121
gacgacttcatcatgagcctgcccgaagagcagtacacctacggccttccgctcacgctc 180

||||||||||||||||||||||||||||||||||||||||||||||||||||||||||||
Coryn:  121
gacgacttcatcatgagcctgcccgaagagcagtacacctacggccttccgctcacgctc 180

READH:  181
ggccacgaaggcgcaggcaaggtcgccgccgtcggcgagggtgtcgaaggtctcgacatc 240

||||||||||||||||||||||||||||||||||||||||||||||||||||||||||||
Coryn:  181
ggccacgaaggcgcaggcaaggtcgccgccgtcggcgagggtgtcgaaggtctcgacatc 240

READH:  241
ggaaccaatgtcgtcgtctacgggccttggggttgtggcaactgttggcactgctcacaa 300
                  |||||||||||||||||||||||| |||||||||||||||||||
||||||||||||||||||||||||
Coryn:  241
ggaaccaatgtcgtcgtctacgggccttggggttgcggcaactgttggcactgctcacaa 300

READH:  301
ggactcgagaactattgctctcgcgcccaagaactcggaatcaatcctcccggtctcggt 360

||||||||||||||||||||||||||||||||||||||||||||||||||||||||||||
Coryn:  301
ggactcgagaactattgctctcgcgcccaagaactcggaatcaatcctcccggtctcggt 360

READH:  361
gcaccggcgcgttggccgagttcatgatcgtcgattctcctcgccaccttgtcccgatc 420

||||||||||||||||||||||||||||||||||||||||||||||||||||||||||||
Coryn:  361
gcaccggcgcgttggccgagttcatgatcgtcgattctcctcgccaccttgtcccgatc 420
```

Fig. 3 (Continued)

```
READH: 421
ggtgacctcgacccggtcaagacggtgccgctgaccgacgccggtctgacgccgtatcac 480
         ||||||||||||||||||||||||||||||||||||||||||||||||||||||||||| : Coryn:
Coryn: 421 ggtgacctcgacccggtcaagacggtgccgctgaccgacgccggtctgacgccgtatcac 480

READH: 481
gcgatcaagcgttctctgccgaaacttcgcggaggctcgtacgcggttgtcattggtacc 540
       ||||||||||||||||||||||||||||||||||||||||||||||||||||||||||||
Coryn: 481
gcgatcaagcgttctctgccgaaacttcgcggaggctcgtacgcggttgtcattggtacc 540

READH: 541
ggcgggctcggccacgtcgccattcagctcctccgtcacctctcggcggcaacggtcatc 600
       ||||||||||||||||||||||||||||   |||||||||||||
Coryn: 541
ggcggtctcggccacgtcgctattcagctcctccgccacctctcggcggcaacggtcatc 600

READH: 601
gctttggacgtgagcgcggacaagctcgaactggcaaccaaggtaggcgctcacgaagtg 660
       ||||||||||||||||||||||||||||||||||||||||||||||||||||||||||||
Coryn: 679
gctttggacgtgagcgcggacaagctcgaactggcaaccaaggtaggcgctcacgaagtg 660

READH: 661
gttctgtccgacaaggacgcggccgagaacgtccgcaagatcactggaagtcaaggcgcc 720
       ||||||||||||||||||||||||||||||||||||||||||||||||||||||||||||
Coryn: 661
gttctgtccgacaaggacgcggccgagaacgtccgcaagatcactggaagtcaaggcgcc 720

READH: 721
gcactggttctcgacttcgtcggctaccagcccaccatcgacaccgcgatggctgtcgcc 780
       |||||||||  |||||||||||||||||||||||||||||||||||||||||||||||||
Coryn: 721
gcattggttctcgacttcgtcggctaccagcccaccatcgacaccgcgatggctgtcgcc 780

READH: 781
ggcgtcggatcagacgtcacgatcgtcgggatcggggacggccaggcccacgccaaagtc 840
       ||||||||||||||||||||||||||||||||||||||||||||||||||||||||||||
Coryn: 781
ggcgtcggatcagacgtcacgatcgtcgggatcggggacggccaggcccacgccaaagtc 840

READH: 841
gggttcttccaaagtccttacgaggcttcggtgacagttccgtattggggtgcccgcaac 900
       ||||||||||||||||||||||||||||||||||||||||||||||||||||||||||||
```

Fig. 3 (Continued)

```
Coryn: 841
gggttcttccaaagtccttacgaggcttcggtgacagttccgtattgggggtgcccgcaac 900

READH: 901 gagttgatcgaattgatcgacctcgcccacgccggcatcttcgacatc-
gcggtggagac 959
            |||||||||||||||||||||||||||||||||||||||||||||||
||||||||||
Coryn: 901
gagttgatcgaattgatcgacctcgcccacgccggcatcttcgacatcggcggtggagac 960

READH:960 cttcagtctcgacaacggtgccgaagcgtatcgacgactggctgccggaacgctaagcgg
          1019
          ||||||||||||||||||||||||||||||||||||||||||||||||||||||| |||||
Coryn:961 cttcagtctcgacaacggtgccgaagcgtatcgacgactggctgccggaacgctcagcgg
          1019

READH: 1020 ccgtgcggttgtggtccctggtctgtag 1047
            ||||||||||||||||||||||||||||
Coryn: 1021 ccgtgcggttgtggtccctggtctgtag 1048
```

Fig. 4

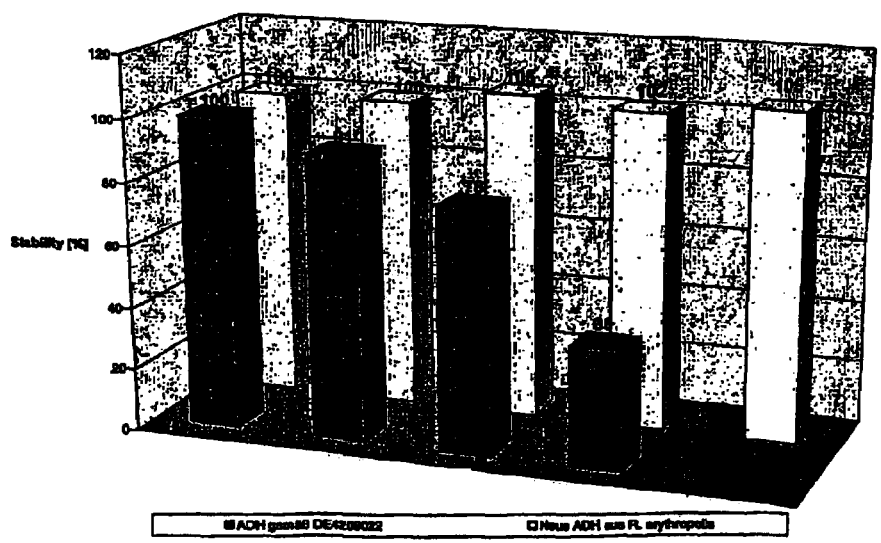

SEQUENCE LISTING

```
<160> NUMBER OF SEQ ID NOS: 18

<210> SEQ ID NO 1
<211> LENGTH: 1047
<212> TYPE: DNA
<213> ORGANISM: Rhodococcus erythropolis
<220> FEATURE:
<221> NAME/KEY: CDS
<222> LOCATION: (1)..(1047)

<400> SEQUENCE: 1
```

```
atg aag gca atc cag tac acg aga atc ggc gcg gaa ccc gaa ctc acg        48
Met Lys Ala Ile Gln Tyr Thr Arg Ile Gly Ala Glu Pro Glu Leu Thr
1               5                   10                  15 gag att ccc aaa ccc gag ccc ggt cca ggt gaa gtg ctc ctg gaa gtc        96
Glu Ile Pro Lys Pro Glu Pro Gly Pro Gly Glu Val Leu Leu Glu Val
            20                  25                  30 acc gct gcc ggc gtc tgc cac tcg gac gac ttc atc atg agc ctg ccc       144
Thr Ala Ala Gly Val Cys His Ser Asp Asp Phe Ile Met Ser Leu Pro
        35                  40                  45 gaa gag cag tac acc tac ggc ctt ccg ctc acg ctc ggc cac gaa ggc       192
Glu Glu Gln Tyr Thr Tyr Gly Leu Pro Leu Thr Leu Gly His Glu Gly
    50                  55                  60 gca ggc aag gtc gcc gcc gtc ggc gag ggt gtc gaa ggt ctc gac atc       240
Ala Gly Lys Val Ala Ala Val Gly Glu Gly Val Glu Gly Leu Asp Ile
65                  70                  75                  80 gga acc aat gtc gtc gtc tac ggg cct tgg ggt tgt ggc aac tgt tgg       288
Gly Thr Asn Val Val Val Tyr Gly Pro Trp Gly Cys Gly Asn Cys Trp
                85                  90                  95 cac tgc tca caa gga ctc gag aac tat tgc tct cgc gcc caa gaa ctc       336
His Cys Ser Gln Gly Leu Glu Asn Tyr Cys Ser Arg Ala Gln Glu Leu
            100                 105                 110 gga atc aat cct ccc ggt ctc ggt gca ccc ggc gcg ttg gcc gag ttc       384
Gly Ile Asn Pro Pro Gly Leu Gly Ala Pro Gly Ala Leu Ala Glu Phe
        115                 120                 125 atg atc gtc gat tct cct cgc cac ctt gtc ccg atc ggt gac ctc gac       432
Met Ile Val Asp Ser Pro Arg His Leu Val Pro Ile Gly Asp Leu Asp
    130                 135                 140 ccg gtc aag acg gtg ccg ctg acc gac gcc ggt ctg acg ccg tat cac       480
Pro Val Lys Thr Val Pro Leu Thr Asp Ala Gly Leu Thr Pro Tyr His
145                 150                 155                 160 gcg atc aag cgt tct ctg ccg aaa ctt cgc gga ggc tcg tac gcg gtt       528
Ala Ile Lys Arg Ser Leu Pro Lys Leu Arg Gly Gly Ser Tyr Ala Val
                165                 170                 175 gtc att ggt acc ggc ggg ctc ggc cac gtc gcc att cag ctc ctc cgt       576
Val Ile Gly Thr Gly Gly Leu Gly His Val Ala Ile Gln Leu Leu Arg
            180                 185                 190 cac ctc tcg gcg gca acg gtc atc gct ttg gac gtg agc gcg gac aag       624
His Leu Ser Ala Ala Thr Val Ile Ala Leu Asp Val Ser Ala Asp Lys
        195                 200                 205 ctc gaa ctg gca acc aag gta ggc gct cac gaa gtg gtt ctg tcc gac       672
Leu Glu Leu Ala Thr Lys Val Gly Ala His Glu Val Val Leu Ser Asp
    210                 215                 220 aag gac gcg gcc gag aac gtc cgc aag atc act gga agt caa ggc gcc       720
Lys Asp Ala Ala Glu Asn Val Arg Lys Ile Thr Gly Ser Gln Gly Ala
225                 230                 235                 240 gca ctg gtt ctc gac ttc gtc ggc tac cag ccc acc atc gac acc gcg       768
Ala Leu Val Leu Asp Phe Val Gly Tyr Gln Pro Thr Ile Asp Thr Ala
                245                 250                 255 atg gct gtc gcc ggc gtc gga tca gac gtc acg atc gtc ggg atc ggg       816
Met Ala Val Ala Gly Val Gly Ser Asp Val Thr Ile Val Gly Ile Gly
            260                 265                 270 gac ggc cag gcc cac gcc aaa gtc ggg ttc ttc caa agt cct tac gag       864
Asp Gly Gln Ala His Ala Lys Val Gly Phe Phe Gln Ser Pro Tyr Glu
        275                 280                 285 gct tcg gtg aca gtt ccg tat tgg ggt gcc cgc aac gag ttg atc gaa       912
Ala Ser Val Thr Val Pro Tyr Trp Gly Ala Arg Asn Glu Leu Ile Glu
    290                 295                 300 ttg atc gac ctc gcc cac gcc ggc atc ttc gac atc gcg gtg gag acc       960
Leu Ile Asp Leu Ala His Ala Gly Ile Phe Asp Ile Ala Val Glu Thr
```

```
                305                 310                 315                 320
ttc agt ctc gac aac ggt gcc gaa gcg tat cga cga ctg gct gcc gga      1008
Phe Ser Leu Asp Asn Gly Ala Glu Ala Tyr Arg Arg Leu Ala Ala Gly
                325                 330                 335 acg cta agc ggc cgt gcg gtt gtg gtc cct ggt ctg tag                  1047
Thr Leu Ser Gly Arg Ala Val Val Val Pro Gly Leu
            340                 345

<210> SEQ ID NO 2
<211> LENGTH: 348
<212> TYPE: PRT
<213> ORGANISM: Rhodococcus erythropolis

<400> SEQUENCE: 2

Met Lys Ala Ile Gln Tyr Thr Arg Ile Gly Ala Glu Pro Glu Leu Thr
 1               5                  10                  15

Glu Ile Pro Lys Pro Glu Pro Gly Pro Gly Glu Val Leu Leu Glu Val
                20                  25                  30

Thr Ala Ala Gly Val Cys His Ser Asp Asp Phe Ile Met Ser Leu Pro
            35                  40                  45

Glu Glu Gln Tyr Thr Tyr Gly Leu Pro Leu Thr Leu Gly His Glu Gly
        50                  55                  60

Ala Gly Lys Val Ala Ala Val Gly Glu Gly Val Glu Gly Leu Asp Ile
65                  70                  75                  80

Gly Thr Asn Val Val Val Tyr Gly Pro Trp Gly Cys Gly Asn Cys Trp
                85                  90                  95

His Cys Ser Gln Gly Leu Glu Asn Tyr Cys Ser Arg Ala Gln Glu Leu
            100                 105                 110

Gly Ile Asn Pro Pro Gly Leu Gly Ala Pro Gly Ala Leu Ala Glu Phe
        115                 120                 125

Met Ile Val Asp Ser Pro Arg His Leu Val Pro Ile Gly Asp Leu Asp
    130                 135                 140

Pro Val Lys Thr Val Pro Leu Thr Asp Ala Gly Leu Thr Pro Tyr His
145                 150                 155                 160

Ala Ile Lys Arg Ser Leu Pro Lys Leu Arg Gly Gly Ser Tyr Ala Val
                165                 170                 175

Val Ile Gly Thr Gly Gly Leu Gly His Val Ala Ile Gln Leu Leu Arg
            180                 185                 190

His Leu Ser Ala Ala Thr Val Ile Ala Leu Asp Val Ser Ala Asp Lys
        195                 200                 205

Leu Glu Leu Ala Thr Lys Val Gly Ala His Glu Val Val Leu Ser Asp
    210                 215                 220

Lys Asp Ala Ala Glu Asn Val Arg Lys Ile Thr Gly Ser Gln Gly Ala
225                 230                 235                 240

Ala Leu Val Leu Asp Phe Val Gly Tyr Gln Pro Thr Ile Asp Thr Ala
                245                 250                 255

Met Ala Val Ala Gly Val Gly Ser Asp Val Thr Ile Val Gly Ile Gly
            260                 265                 270

Asp Gly Gln Ala His Ala Lys Val Gly Phe Phe Gln Ser Pro Tyr Glu
        275                 280                 285

Ala Ser Val Thr Val Pro Tyr Trp Gly Ala Arg Asn Glu Leu Ile Glu
    290                 295                 300

Leu Ile Asp Leu Ala His Ala Gly Ile Phe Asp Ile Ala Val Glu Thr
305                 310                 315                 320

Phe Ser Leu Asp Asn Gly Ala Glu Ala Tyr Arg Arg Leu Ala Ala Gly
```

325                 330                 335
Thr Leu Ser Gly Arg Ala Val Val Val Pro Gly Leu
            340                 345

<210> SEQ ID NO 3
<211> LENGTH: 27
<212> TYPE: DNA
<213> ORGANISM: Artificial sequence
<220> FEATURE:
<223> OTHER INFORMATION: synthetic oligonucleotide

<400> SEQUENCE: 3
atgaaggcsa tccagtacac scgsatc                                        27

<210> SEQ ID NO 4
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 4
gccggtacca aygasaascg cgta                                           24

<210> SEQ ID NO 5
<211> LENGTH: 27
<212> TYPE: DNA
<213> ORGANISM: Artificial sequence
<220> FEATURE:
<223> OTHER INFORMATION: synthetic oligonucleotide

<400> SEQUENCE: 5
atccagtaca cgcgcatcgg cgcggaa                                        27

<210> SEQ ID NO 6
<211> LENGTH: 27
<212> TYPE: DNA
<213> ORGANISM: Artificial sequence
<220> FEATURE:
<223> OTHER INFORMATION: synthetic oligonucleotide

<400> SEQUENCE: 6
gcctccgcga agtttcggca gagaacg                                        27

<210> SEQ ID NO 7
<211> LENGTH: 30
<212> TYPE: DNA
<213> ORGANISM: Artificial sequence
<220> FEATURE:
<223> OTHER INFORMATION: synthetic oligonucleotide

<400> SEQUENCE: 7
gcggaattca tgaaggcaat ccagtacacg                                     30

<210> SEQ ID NO 8
<211> LENGTH: 30
<212> TYPE: DNA
<213> ORGANISM: Artificial sequence
<220> FEATURE:
<223> OTHER INFORMATION: synthetic oligonucleotide

<400> SEQUENCE: 8
cgcaagcttc tacagaccag ggaccacaac                                     30

<210> SEQ ID NO 9

```
<211> LENGTH: 42
<212> TYPE: DNA
<213> ORGANISM: Artificial sequence
<220> FEATURE:
<223> OTHER INFORMATION: synthetic oligonucleotide

<400> SEQUENCE: 9
gaggtcggtc atatgaaggc aatccagtac acgcgtatcg gc                           42

<210> SEQ ID NO 10
<211> LENGTH: 30
<212> TYPE: DNA
<213> ORGANISM: Artificial sequence
<220> FEATURE:
<223> OTHER INFORMATION: synthetic oligonucleotide

<400> SEQUENCE: 10
cgcggatccc tacagaccag ggaccacaac                                         30

<210> SEQ ID NO 11
<211> LENGTH: 39
<212> TYPE: DNA
<213> ORGANISM: Artificial sequence
<220> FEATURE:
<223> OTHER INFORMATION: synthetic oligonucleotide

<400> SEQUENCE: 11
ggtgaattca tgaaggcaat ccagtacacg cgtatcggc                               39

<210> SEQ ID NO 12
<211> LENGTH: 42
<212> TYPE: DNA
<213> ORGANISM: Artificial sequence
<220> FEATURE:
<223> OTHER INFORMATION: synthetic oligonucleotide

<400> SEQUENCE: 12
cgcaagcttc tagtggtggt ggtggtggtg cagaccaggg ac                           42

<210> SEQ ID NO 13
<211> LENGTH: 510
<212> TYPE: DNA
<213> ORGANISM: Artificial sequence
<220> FEATURE:
<223> OTHER INFORMATION: synthetic oligonucleotide

<400> SEQUENCE: 13
atccagtaca cgagaatcgg cgcggaaccc gaactcacgg agattcccaa acccgagccc        60
ggtccaggtg aagtgctcct ggaagtcacc gctgccggcg tctgccactc ggacgacttc       120
atcatgagcc tgcccgaaga gcagtacacc tacggccttc cgctcacgct cggccacgaa       180
ggcgcaggca aggtcgccgc cgtcggcgag ggtgtcgaag gtctcgacat cggaaccaat       240
gtcgtcgtct acgggccttg gggttgtggc aactgttggc actgctcaca aggactcgag       300
aactattgct ctcgcgccca agaactcgga atcaatcctc ccggtctcgg tgcacccggc       360
gcgttggccg agttcatgat cgtcgattct cctcgccacc ttgtcccgat cggtgacctc       420
gacccggtca agacggtgcc gctgaccgac gccggtctga cgccgtatca cgcgatcaag       480
cgttctctgc cgaaacttcg cggaggctcg                                        510

<210> SEQ ID NO 14
<211> LENGTH: 32
<212> TYPE: PRT
<213> ORGANISM: Artificial sequence
```

-continued

```
<220> FEATURE:
<223> OTHER INFORMATION: conservative regions

<400> SEQUENCE: 14

Glu Pro Glu Leu Thr Glu Ile Pro Lys Pro Glu Pro Gly Pro Gly Glu
1               5                   10                  15

Val Leu Leu Glu Val Thr Ala Ala Gly Val Cys His Ser Asp Asp Phe
                20                  25                  30

<210> SEQ ID NO 15
<211> LENGTH: 15
<212> TYPE: PRT
<213> ORGANISM: Artificial sequence
<220> FEATURE:
<223> OTHER INFORMATION: conservative regions

<400> SEQUENCE: 15

Cys Gly Asn Cys Trp His Cys Ser Gln Gly Leu Glu Asn Tyr Cys
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: conservative regions

<400> SEQUENCE: 16

Cys Gly Asn Cys Trp His Cys Ser Gln Gly Leu Glu Asn Tyr Cys
1               5                   10                  15

<210> SEQ ID NO 17
<211> LENGTH: 48
<212> TYPE: PRT
<213> ORGANISM: Artificial sequence
<220> FEATURE:
<223> OTHER INFORMATION: conservative regions

<400> SEQUENCE: 17

His Leu Val Pro Ile Gly Asp Leu Asp Pro Val Lys Thr Val Pro Leu
1               5                   10                  15

Thr Asp Ala Gly Leu Thr Pro Tyr His Ala Ile Lys Arg Ser Leu Pro
                20                  25                  30

Lys Leu Arg Gly Gly Ser Tyr Ala Val Val Ile Gly Thr Gly Gly Leu
            35                  40                  45

<210> SEQ ID NO 18
<211> LENGTH: 1047
<212> TYPE: DNA
<213> ORGANISM: Corynebacterium sp. ST-10

<400> SEQUENCE: 18
atgaaggcga tccagtacac gcgaatcggc gcggaacccg aactcacgga gattcccaaa      60
cccgagcccg gtccaggtga agtgctcctg gaagtcaccg ctgctggcgt ctgccactcg    120
gacgacttca tcatgagcct gcccgaagag cagtacacct acggccttcc gctcacgctc    180
ggccacgaag gcgcaggcaa ggtcgccgcc gtcggcgagg gtgtcgaagg tctcgacatc    240
ggaaccaatg tcgtcgtcta cgggccttgg ggttgcggca actgttggca ctgctcacaa    300
ggactcgaga actattgctc tcgcgcccaa gaactcggaa tcaatcctcc cggtctcggt    360
gcacccggcg cgttggccga gttcatgatc gtcgattctc ctcgccacct tgtcccgatc    420
ggtgacctcg acccggtcaa gacggtgccg ctgaccgacg ccggtctgac gccgtatcac    480
```

-continued

```
gcgatcaagc gttctctgcc gaaacttcgc ggaggctcgt acgcggttgt cattggtacc      540
ggcggtctcg gccacgtcgc tattcagctc ctccgccacc tctcggcggc aacggtcatc      600
gctttggacg tgagcgcgga caagctcgaa ctggcaacca aggtaggcgc tcacgaagtg      660
gttctgtccg acaaggacgc ggccgagaac gtccgcaaga tcactggaag tcaaggcgcc      720
gcactggttc tcgacttcgt cggctaccag cccaccatcg acaccgcgat ggctgtcgcc      780
ggcgtcggat cagacgtcac gatcgtcggg atcggggacg gccaggccca cgccaaagtc      840
gggttcttcc aaagtcctta cgaggcttcg gtgacagttc cgtattgggg tgcccgcaac      900
gagttgatcg aattgatcga cctcgcccac gccggcatct tcgacatcgc ggtggagacc      960
ttcagtctcg acaacggtgc cgaagcgtat cgacgactgg ctgccggaac gctcagcggc     1020
cgtgcggttg tggtccctgg tctgtag                                          1047
```

ADH FROM *RHODOCOCCUS ERYTHROPOLIS*

The present invention deals with an alcohol dehydrogenase (ADH, RE-ADH) from the organism *Rhodococcus erythropolis*. The invention is also directed, inter alia, at a process for preparing polypeptides with alcohol dehydrogenase activity and the use thereof. A special whole cell catalyst or a coupled enzymatic reaction system is also claimed.

The production of optically active organic compounds. e.g. alcohols and α-amino acids, using a biocatalytic route is becoming increasingly important. The coupled use of two dehydrogenases with cofactor regeneration has been demonstrated as a route to the industrial scale synthesis of these compounds (DE19753350).

Reaction scheme 1:

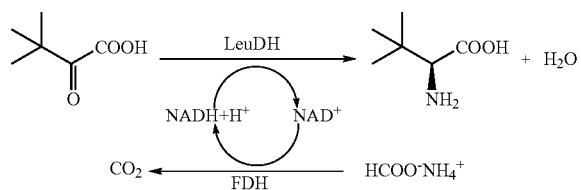

In situ regeneration of NADH using NAD-dependent formate dehydrogenase during the reductive amination of trimethylpyruvate to give L-tert-leucine (Bommarius et al. *Tetrahedron: Asymmetry* 1995, 6, 2851-2888).

Alcohol dehydrogenases (ADHs) are of similar interest in this connection, but they enable, in a parallel coupled enzymatic system, inter alia the preparation of enantiomerically enriched alcohols starting from ketones or racemic alcohols (DE10037101; for a an up-to-date comprehensive review of the prior art, see: W. Hummel, *Adv. Biochem. Engineering/Biotechnology* 1997, 58, 145-184.)).

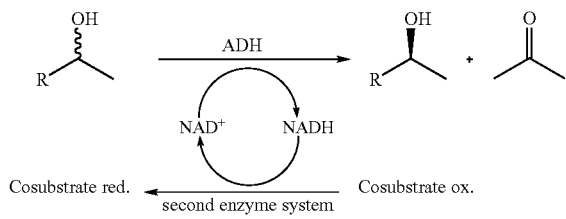

ADHs are classified in class E.C. 1.1.1.1 and thus belong to the so-called oxidoreductases. They are found in a number of organisms (Enzyme Catalysis in Organic Synthesis, Ed.: K. Drauz and H. Waldmann, 1995, VCH, Vol. II, 595ff). So-called "broadband" enzymes which react stereoselectively on a wide range of substrates are of interest.

Three different ADHs, from yeast (YADH), from horse liver (HLADH) and from *Thermoanaerobium brockii* (TBADH), which are used to prepare alcohols are already commercially available for preparative applications on a laboratory scale. In addition, other ADHs can be purchased but these are more likely, as their names suggest, to react with specific substrates such as e.g. a few steroid dehydrogenases which react preferentially with alcohol groups in steroid structures or glycerol dehydrogenase which reacts with glycerine or lastly also several sugar-reacting enzymes such as glucose DH.

Most ADHs hitherto disclosed in the literature are "S-specific" (wherein the terms S and R may also sometimes be reversed in the nomenclature for technical reasons). According to our knowledge, however, the ADHs from *Lactobacillus* strains are R-specific (see C. W. Bradshaw, W. Hummel, C.-H. Wong, *J. Org. Chem.* 1992, 57, 1532.) as well as another ADH disclosed in the literature, from *Pseudomonas* (P. Hildebrandt, T. Riermeier, J. Altenbuchner, U. T. Bornscheuer, *Tetrahedron: Asymmetry* 2001, 12, 1207.), which was recently described by the study group Altenbuchner and Bornscheuer. The study group including Keinan and Lamed reported on an ADH from *Thermoanaerobium brockii* (E. Keinan, E. K. Hafeli, K. K. Seth, R. Lamed, *J. Am. Chem. Soc.* 1986, 108, 162.) which shows (R)-specificity for small substrates but is (S)-specific for large substrates.

Although a large number of representatives of (S)-specific alcohol dehydrogenases are known, their industrial suitability is generally very restricted. This demonstrates not least the very few industrial processes which actually use these enzymes in contrast to the large number of known ADHs. The (S)-ADH from yeast is a NAD-dependent enzyme. It is very inexpensive, but substantially converts only primary alcohols (or aldehydes), so this enzyme is not very useful for the preparation of chiral alcohols. In addition, this enzyme is extremely sensitive and characterised by a high degree of instability, in particular with regard to organic solvents. The NAD-dependent (S)-ADH from horse liver (HLADH) is undoubtedly the most frequently used alcohol dehydrogenase used hitherto, particularly in the academic field, as demonstrated by the large number of publications using this enzyme (see e.g. a review in: K. Faber, *Biotransformations in Organic Chemistry*, 4th edition, Springer-Verlag, 2000, p. 184 et seq.). Unfortunately, this enzyme is not really suitable for industrial use due to the lack of availability. In addition, the (S)-ADH from horse liver is very expensive (1 U costs about 0.5 Euro), and is not currently available in recombinant form. Also, the substrate spectrum preferably comprises cyclic ketones; ketones with aromatic side chains (the acetophenone type) are not converted. However, this class of substances comprising aromatic ketones is of particular importance from an industrial point of view due to the large number of applications as key intermediates in the pharmaceutical sector (for selected examples, see: a) R. A. Holdt, S. R. Rigby (Zeneca Limited), U.S. Pat. No. 5,580,764, 1996; b) T. J. Blacklock, P. Sohar, J. W. Butcher, T. Lamanec, E. J. J. Grabowski, *J. Org. Chem.* 1993, 58, 1672-1679; c) R. A. Holdt, *Chimica Oggi—Chemistry Today* 1996, 9, 17-20; d) F. Bracher, T. Litz, *Arch. Pharm.* 1994, 327, 591-593; e) S. Y. Sit, R. A. Parker, I. motoc, W. Han, N. Balasubramanian, *J. Med. Chem.* 1990, 33, 2982-2999; f) A. zaks, D. R. Dodds, *Drug Discovery Today* 1997, 2, 513-530). NADP-dependent (NADP is 5-10 times more expensive than NAD) ADH from the bacterium *Thermoanaerobium brockii* (TBADH), on the other hand, is available in the recombinant form. However, its substrate spectrum is restricted to aliphatic ketones. Ketones with aromatic side chains (the acetophenone type), for example, are not converted.

Apart from the use of isolated enzymes, the use of whole cell catalysts which contain alcohol dehydrogenases is also known, wherein there are disadvantages in principle as compared with the use of isolated enzymes. These disadvantages, which are described, inter alia, in K. Faber, *Biotransformations in Organic Chemistry*, 4th edition, Springer-Verlag, 2000, p. 193 et seq., include low productivities and yields in microorganism-catalysed reactions as compared with isolated enzymes. For example, the reaction times when using baker's yeast, which is probably the most popular whole cell catalyst used, are not infrequently in the region of several days for reaction. Another disadvantage is the difficult product working-up process (separation of the added carbon source, cell material and secondary products) as well as the problems involved due to the fact that several ADHs are usually present in the cells, these acting at the same time and often resulting in undesired secondary reactions and reduced yields and enantioselectivities for the desired products. Nevertheless, some examples are known from the literature where native whole cell catalysts are used on a large scale, without such processes generally reaching an industrial scale (=tonne scale). For example, the Zeneca Life-Science Co. (R. A. Holdt, S. R. Rigby (Zeneca Ltd.), U.S. Pat. No. 5,580,764, 1996) describes the conversion of dihydro-6-methyl-4-thieno-thiopyran-4-one-7,7-dioxide to the corresponding 4-hydroxy compound using an ADH from *Neurospora crassa* (a filamentous fungus), wherein the enzyme is not isolated but, as mentioned above, whole cells are used. Bristol-Myers-Squib converted ethyl 6-benzyloxy-3,5-dioxo-hexanoate to the corresponding 3,5-dihydroxy compound using an enzyme present in the cell extract from *Acinetobacter calcoaceticus* (bacterium) (R. N. Patel, C. G. McNamee, A. Banerjee, L. J. Szarka (E. R. Squibb & Sons), EP569998, 1993). Furthermore, the conversion of methyl 4-chloro-3-oxo-butyrate to the corresponding 3-hydroxy compound using an ADH from *Geotrichum candidum* (a yeast) has been described (Patel, R. N., McNamee, C. G., Banerjee, A., Howell, J. M., Robinson, R. S., Szarka, L. J., *Enzyme Microb. Technol.* 1992, 14, 731).

Eli Lilly published the transformation of 3,4-methylenedioxyacetophenone to give the corresponding alcohol using an ADH from *Zygosaccharomyces rouxii* (a yeast) (J. T. Vicenzi, M. J. Zmijewski, M. R. Reinhard, B. E. Landen, W. L. Muth, P. G. Marler, *Enzyme Microb. Technol.* 1997, 20, 494).

Merck converted a pyridine derivative with *Candida sorbophila* (a yeast) (Chartrain, M., Chung, J., Roberge, C. (Merck & Co., Inc.), U.S. Pat. No. 5,846,791, 1998).

A Japanese publication describes the reduction of methyl 4-chloro-3-oxo-butyrate with ADH in a recombinant whole cell catalyst. A suitable ADH (non-commercial "ketoreductase") and a coenzyme-regenerating enzyme are cloned together in *E. coli* cells (Kataoka, M., et al. *Appl. Microbiol. Biotechnol.* 1997, 48, 699; Kataoka, M., et al., *Biosci., Biotechnol., Biochem.* 1998, 62, 167).

With reference to (S)-specific enzymes, a (S)-ADH from the organism *Rhodococcus erythropolis* is already known from the patent application DE4209022. However, this is obviously an enzymatic system which has little thermal stability and has a temperature optimum at 45° C. after incubation for 10 minutes. Since thermal stability is directly linked to operational stability and stability in solvents (Suzuki, Y., K. Oishi, H. Nakano and T. Nagayama. *Appl. Microbiol. Biotechnol.* 26: 546), only a moderate suitability for industrial processes would be expected for the mesophilic enzyme described in that document.

Thus, there is obviously still a need for further, optionally improved, ADHs which can be used in industrial syntheses. Thus, the object of the present invention was to provide further alcohol dehydrogenases (ADHs), or the nucleic acids coding for them, with optionally improved properties as compared with known enzymes. In particular, the ADHs should be capable of effective use on an industrial scale to prepare enantiomer-enriched alcohols so that these types of production processes can be performed advantageously, from an economic and ecological point of view, on a commercial scale, this requiring an above-average ADH with regard to selectivity, stability and/or activity.

This object is achieved in accordance with the Claims. Claim 1 relates to specific nucleic acids, Claim 2 to the associated polypeptides. Claims 3 and 4 are directed at primers and vehicles for the nucleic acids according to the invention. Claim 5 protects a mutagenesis process with the aid of which improved polypeptides can be obtained. Claim 6 relates to the polypeptides and nucleic acid sequences themselves derivable therefrom. Claims 7 and 8 are directed at the use of the polypeptides and nucleic acids prepared or cited in this way, while Claims 9 to 11 are directed at specific whole cell catalysts. Finally Claims 12 and 13 provide reaction systems modified with enzymes according to the invention. Claim 14 relates to the use of the whole cell catalyst according to the invention, while Claim 15 protects a vector according to the invention. Claims 16 and 17 are then again directed at the use of certain vectors.

Making available an isolated nucleic acid sequence which codes for a polypeptide with alcohol dehydrogenase activity chosen from the group:

a) a nucleic acid sequence with the sequence given in Seq. ID NO: 1,
b) a nucleic acid sequence which, under stringent conditions, hybridises with the nucleic acid sequence in accordance with Seq. ID NO: 1 or the sequence complementary thereto,
c) a nucleic acid sequence which is at least 91% homologous with Seq. ID NO: 1,
d) a nucleic acid sequence which codes for a polypeptide which is at least 84% homologous with the amino acid sequence given in Seq. ID NO: 2, without the activity and/or selectivity and/or stability of the polypeptide being substantially reduced when compared with the polypeptide in Seq. ID NO: 2,
e) a nucleic acid sequence coding for a polypeptide with improved activity and/or selectivity and/or stability as compared with the polypeptide in Seq. ID NO: 2, prepared by
  i) mutagenesis of Seq. ID NO: 1,
  ii) cloning the nucleic acid sequence obtainable from i) in a suitable vector followed by transformation in a suitable expression system and
  iii) detection of the critical polypeptide with improved activity and/or selectivity and/or stability, provides the opportunity, in a preferred manner, to be able to prepare, in adequate amounts and using recombinant techniques, the enzymes required for an enzymatic industrial process to produce enantiomer-enriched compounds. Using the nucleic acid sequences, it is possible to obtain the polypeptides in high yields from rapidly growing host organisms. In addition to an unusually wide substrate spectrum, the polypeptides according to the invention are also, contrary to expectation, heat-resistant.

They convert, inter alia, aliphatic and aromatic ketones, aldehydes and 2- or 3-ketoesters. Unusual and unexpected, as mentioned, is the fact that the polypeptides coded by the nucleic acid sequences according to the invention exhibit virtually no deactivation within 15 minutes at 65° C., although they originate from a *bacterium* which itself no longer grows at 37° C. and therefore is not thermophilic. In addition to this very high thermal stability, which is advantageously accompanied by high operational stability and solvent-resistance (Suzuki, Y. et al. *Appl. Microbiol. Bio-* technol. 26: 546 (see above)), the present polypeptide, and thus also the nucleic acid sequence coding for this enzyme, differs from the enzyme mentioned in DE4209022 in structure and size. Whereas the 4 subunits in the polypeptide according to the invention each have a molar mass of 39 kDa (±2 kDa), the 2 subunits in DE4209022 have a molar mass of 72 kDa (±5).

In the present invention, therefore, in addition to the original nucleic acid sequences, those which hybridise under stringent conditions with the nucleic acid sequence according to the invention or sequences which are complementary thereto and also others which have been improved by suitable methods of mutagenesis are also claimed.

The procedure to improve the nucleic acids according to the invention or the polypeptides coded by them using the methods of mutagenesis is sufficiently well-known to a person skilled in the art. Suitable methods of mutagenesis are all the methods available for this purpose to a person skilled in the art. In particular these include saturation mutagenesis, random mutagenesis, in vitro recombination methods and site-directed mutagenesis (Eigen, M. and Gardiner, W., Evolutionary molecular engineering based on RNA replication, *Pure Appl. Chem.* 1984, 56, 967-978; Chen, K. and Arnold, F., Enzyme engineering for non-aqueous solvents: random mutagenesis to enhance activity of subtilisin E in polar organic media. *Bio/Technology* 1991, 9, 1073-1077; Horwitz, M. and Loeb, L., Promoters Selected From Random DNA-Sequences, *Proc Natl Acad Sci USA* 83, 1986, 7405-7409; Dube, D. and L. Loeb, Mutants Generated By The Insertion Of Random Oligonucleotides Into The Active-Site Of The Beta-Lactamase Gene, *Biochemistry* 1989, 28, 5703-5707; Stemmer, P. C., Rapid evolution of a protein in vitro by DNA shuffling, *Nature* 1994, 370, 389-391 and Stemmer, P. C., DNA shuffling by random fragmentation and reassembly: In vitro recombination for molecular evolution. *Proc Natl Acad Sci USA* 91, 1994, 10747-10751).

The new nucleic acid sequences obtained are cloned in a host organism (see below for literature references), using the methods cited below, and the polypeptides expressed in this way are detected and then isolated using suitable screening methods. For the purposes of detection, all the possible detection reactions for the molecules formed with this polypeptide are basically suitable. In particular, a photometric test via the NADH formed or consumed, HPLC or GC methods can be used here to detect the alcohols formed with this enzyme. In addition, to detect new polypeptides modified by means of genetic engineering techniques, gel electrophoretic methods of detection or methods of detection using antibodies are also suitable.

As mentioned above, the invention also covers nucleic acid sequences which hybridise under stringent conditions with the single-strand nucleic acid sequences according to the invention or single-strand nucleic acid sequences which are complementary thereto. For example, the gene probe in accordance with Seq. 13 or the primer mentioned in Seq. 3-12 are regarded as such sequences.

The expression "under stringent conditions" is to be understood here in the same way as is described in Sambrook et al. (Sambrook, J.; Fritsch, E. F. and Maniatis, T. (1989), Molecular cloning: a laboratory manual, $2^{nd}$ ed., Cold Spring Harbor Laboratory Press, New York). Stringent hybridisation in accordance with the present invention is preferably present when, after washing for one hour with 1×SSC (150 mM sodium chloride, 15 mM sodium citrate, pH 7.0) and 0.1% SDS (sodium dodecylsulfate) at 50° C., preferably at 55° C., more preferably at 62° C. and most preferably at 68° C. and more preferably for one hour with 0.2×SSC and 0.1% SDS at 50° C., preferably at 55° C., more preferably at 62° C. and most preferably at 68° C., a positive hybridisation signal is still observed.

Furthermore, the present application provides polypeptides (enzymes) chosen from the group
a) polypeptides coded by a nucleic acid sequence according to the invention,
b) polypeptides containing a sequence in accordance with Seq. ID NO: 2,
c) polypeptides which are >82% homologous to the polypeptide in Seq. ID NO: 2, without the activity and/or selectivity and/or stability of the polypeptide being substantially reduced when compared with the polypeptide in Seq. ID NO: 2.

Polypeptides according to the invention are very easy to use in industrial processes due to the stability indicated above and the wide substrate spectrum.

In a next development, the invention provides plasmids or vectors containing one or more of the nucleic acid sequences according to the invention.

Suitable plasmids or vectors are in principle all embodiments which are available to a person skilled in the art for this purpose. These types of plasmids and vectors can be found e.g. in Studier et al. (Studier, W. F.; Rosenberg A. H.; Dunn J. J.; Dubendroff J. W.;, Use of the T7 RNA polymerase to direct expression of cloned genes, *Methods Enzymol.* 1990, 185, 61-89) or in company brochures issued by Novagen, Promega, New England Biolabs, Clontech or Gibco BRL. Other preferred plasmids and vectors can be found in: Glover, D. M. (1985), DNA cloning: a practical approach, Vol. I-III, IRL Press Ltd., Oxford; Rodriguez, R. L. and Denhardt, D. T (eds) (1988), Vectors: a survey of molecular cloning vectors and their uses, 179-204, Butterworth, Stoneham; Goeddel, D. V., Systems for heterologous gene expression, *Methods Enzymol.* 1990, 185, 3-7; Sambrook, J.; Fritsch, E. F. and Maniatis, T. (1989), Molecular cloning: a laboratory manual, $2^{nd}$ ed., Cold Spring Harbor Laboratory Press, New York.

Plasmids with which the gene constructs containing nucleic acids according to the invention can be cloned in a very preferred manner in the host organism are: pUC18 (Roche Biochemicals), pKK-177-3H (Roche Biochemicals), pBTac2 (Roche Biochemicals), pKK223-3 (Amersham Pharmacia Biotech), pKK-233-3 (Stratagene) or pET (Novagen), or pKA1 (FIG. 1).

Likewise, the invention also provides microorganisms containing one or more of the nucleic acid sequences according to the invention.

The microorganism in which the plasmids which contain the nucleic acid sequences according to the invention are cloned is used to multiply and obtain a sufficient amount of the recombinant enzyme. The processes used for this purpose are well-known to a person skilled in the art (Sambrook, J.; Fritsch, E. F. and Maniatis, T. (1989), Molecular cloning: a laboratory manual, $2^{nd}$ ed., Cold Spring Harbor Laboratory Press, New York). Microorganisms which may be referred to are in principle all organisms known to a person skilled in the art which are suitable for this purpose such as e.g. yeasts such as *Hansenula polymorpha*, *Pichia* sp., *Saccharomyces cerevisiae*, prokaryotes, *E. coli*, *Bacillus*

*subtilis* or eukaryontes, such as mammal cells, insect cells. Strains of *E. coli* are preferably used for this purpose. The following are very particularly preferred: *E. coli* XL1 Blue, NM 522, JM101, JM109, JM105, RR1, DH5α, TOP 10⁻ HB101. Plasmids with which the gene construct containing the nucleic acid according to the invention is preferably cloned, in the host organism are mentioned above.

A further aspect of the invention provides primers for preparing the gene sequences according to the invention by means of all types of PCR. Sense and antisense primers coding for the corresponding amino acid sequences, or complementary DNA sequences, are included. Suitable primers may be obtained in principle by processes known to a person skilled in the art. Finding the primers according to the invention is performed by comparison with known DNA sequences or by translating the amino acid sequences detected by eye in the preferred codon of the organism under consideration (e.g. for *Streptomyces*: Wright F. and Bibb M. J. (1992), Codon usage in the G+C-rich *Streptomyces* genome, Gene 113, 55-65). Common features in the amino acid sequence of proteins from so-called superfamilies are also of use in this regard (Firestine, S. M.; Nixon, A. E.; Benkovic, S. J. (1996), Threading your way to protein function, Chem. Biol. 3, 779-783). Further information on this topic can be found in Gait, M. J. (1984), Oligonucleotide synthesis: a practical approach, IRL Press Ltd., Oxford; Innis, M. A.; Gelfound, D. H.; Sninsky, J. J. and White, T. J. (1990), PCR Protocols: A guide to methods and applications, Academic Press Inc., San Diego. The following primers are extremely preferred:

```
5'-Primer:
                                              (Seq. 3)
ATG AAG GCG(C) ATC CAG TAG ACG(C) CGG(C) ATC 3'-Primer:
                                              (Seq. 4)
GCC GGT ACC AAT(C) GAC(G) AAC(G) CGC GTA 5'-Primer:
                                              (Seq. 5)
ATC CAG TAC ACG CGC ATC GGC GCG GAA 3'-Primer:
                                              (Seq. 6)
GCC TCC GCG AAG TTT CGG CAG AGA ACG 5'-Primer:
                                              (Seq. 7)
GCG GAA TTC ATG AAG GCA ATC CAG TAC ACG 3'-Primer:
                                              (Seq. 8)
CGC AAG CTT CTA CAG ACC AGG GAC CAC AAC 5'- Primer:
                                              (Seq. 9)
GAG GTC GGT CAT ATG AAG GCA ATC CAG TAC ACG CGT
ATC GGC 3'-Primer:
                                              (Seq. 10)
CGC GGA TCC CTA CAG ACC AGG GAC CAC AAC 5'-Primer:
                                              (Seq. 11)
GGT GAA TTC ATG AAG GCA ATC CAG TAC ACG CGT ATC
GGC 3'-Primer:
                                              (Seq. 12)
CGC AAG CTT CTA GTG GTG GTG GTG GTG GTG CAG ACC
AGG GAC
```

In a further development, the present invention provides a process for preparing improved rec-polypeptides with alcohol dehydrogenase activity starting from nucleic acid sequences according to the invention, wherein the following protocol is applied:

a) the nucleic acid sequences are subjected to mutagenesis, b) the nucleic acid sequences obtainable from a) are cloned in a suitable vector and these are then transferred to a suitable expression system and c) the polypeptides with improved activity and/or selectivity and/or stability formed are detected and isolated.

The invention also provides rec-polypeptides or nucleic acid sequences coding for these which are obtainable by a process like the one just described.

Preparation of the nucleic acid sequences required to produce the improved rec-polypeptides and their expression in hosts is described below and accordingly applies here.

The polypeptides and rec-polypeptides according to the invention are preferably used to prepare chiral enantiomer-enriched organic compounds such as e.g. sec-alcohols with a stereogenic centre.

Surprisingly, the new type of alcohol dehydrogenases and previously known alcohol dehydrogenases, e.g. ADHs from *R. erythropolis*, exhibit very different biochemical properties, in particular with regard to the substrate pattern and also to the enantioselectivity produced. The new ADH is shown to be particularly suitable for preparing aromatic secondary alcohols, which leads to a high level of industrial attractiveness for the new ADH, simply because of the commercial importance of this class of substances.

In the following in particular the differences and advantages when compared with the previous ADHs from *R. erythropolis* are described.

The alcohol dehydrogenase from *R. erythropolis* now claimed exhibits significant differences when compared with earlier ADHs (described for example in DE 4209022, 1991, J. Peters et al., *J. Biotechnol.* 1994, 33, 283 and J. Peters, Dissertation, Univ. Düsseldorf, 1993) which have been used either directly from the crude extract or partially purified. These differences relate, as mentioned above, both to physical properties such as structure, thermal stability and stability in organic media and also to biochemical properties, in particular with respect to substrate acceptance.

The significant differences in the biochemical characteristics (substrate acceptance) of the "new" ADH from *R. erythropolis*, when compared with the already known ADHs mentioned above (=prior art), are described below. In the Tables given below, this is explained using exemplary examples and also graphically. In this case, as is normal, the measured activity for one compound is set at 100% and the activity/activities of the other compound(s) is determined in relation thereto. From the relative activities when compared with other substrates, it can then be recognised whether such another substrate is accepted to a greater or lesser extent.

A first significant example is herewith shown in Table 1. In this case, the activity measured each time for p-methylacetophenone was set at 100%. Surprisingly, it was shown that the new ADH led to a greatly improved acceptance with the substrate p-chloroacetophenone, with a relative activity of 189%. In contrast, a reduced activity in comparison to p-methylacetophenone, only 81%, was determined for the earlier ADH (described in DE 4209022, 1991).

TABLE 1

| | ADH in accordance with DE 42090922 | New ADH expr. in E. coli |
|---|---|---|
| p-chloroacetophenone | 81% | 189% |
| p-methylacetophenone | 100% | 100% |

Note:
The activities given in this table are relative activities and are given with reference to the activity measured for p-methylacetophenone Another interesting comparison is shown in Table 2. Here, the relative activities are given with respect to p-fluoroacetophenone. In this case it is shown that the new ADH preferentially accepts the substrate p-methoxyacetophenone (rel. activity: 195%), whereas the opposite effect is observed for the previously known ADH (in accordance with DE 4209022, 1991) (rel. activity of only 90% for p-methoxyacetophenone compared with 100% for p-fluoroacetophenone).

TABLE 2

| | ADH in accordance with DE 42090922 | New ADH expr. in E. Coli |
|---|---|---|
| p-methoxyacetophenone | 90% | 195% |
| p-fluoroacetophenone | 100% | 100% |

Note:
The activities given in this table are relative activities and are given with reference to the activity measured for p-fluoroacetophenone.

However, significant differences are not restricted to the area of differently substituted aromatic ketones, but are also detected just in a general comparison with aliphatic β-ketoesters (Table 3). Thus, β-ketoethyl esters are far more readily accepted by the already known form of ADH (from J. Peters, *Dissertation*, 1993) than is p-chloroacetophenone as a representative of aromatic ketones (250% vs. 100%). Even the much less readily accepted ketoester substrate methyl acetoacetate has the same activity as p-chloracetophenone. The opposite trend is exhibited by the new form of ADH: here, in comparison to the methyl ester, p-chloroacetophenone has more than 9 times the activity (909% vs. 100%). Even in comparison to the β-ketoethyl ester, p-chloroacetophenone has a higher activity when using the new ADH (909% vs. 773%). Thus, this example also proves the significant qualitative change in substrate acceptance when comparing the new ADH with the previously known ADHs in accordance with J. Peters, *Dissertation*, University of Düsseldorf, 1993.

TABLE 3

| | ADH in accordance with J. Peters, Dissertation | New ADH expr. in E. coli |
|---|---|---|
| methyl acetoacetate | 100% | 100% |
| ethyl acetoacetate | 250% | 773% |
| p-chloroacetophenone | 100% | 909% |

Note:
The activities given in this table are relative activities and are given with reference to the activity measured for methyl acetoacetate.

Finally, it may be mentioned that significant qualitative differences with regard to substrate acceptance are also found for ketones functionalised in a different way. This is shown for example by a comparison of pure long-chain alkyl ketones with phenoxyacetone, as a representative of a heteroatom-substituted dialkyl ketone (Table 4).

TABLE 4

| | ADH in accordance with J. Peters, Dissertation | New ADH expr. in E. Coli |
|---|---|---|
| 2-heptanone | 100% | 100% |
| 2-decanone | 79% | 76% |
| phenoxyacetone | 71% | 126% |

Note:
The activities given in this table are relative activities and are given with reference to the activity measured for 2-heptanone.

Thus, the substrate pattern for the known form of ADH from J. Peters, *Dissertation*, 1993 clearly demonstrates a preference for long-chain alkyl ketones. Higher activities were determined for both 2-heptanone (100%) and 2-decanone (79%) than for phenoxyacetone (71%). The new ADH, however, exhibits a completely different substrate pattern. Here, the highest activity by far, 126%, was determined for phenoxyacetone, while the alkyl ketones had much lower activities (100% and 76%). The trend within the 2-alkyl ketones with a preference for C7-ketones rather than C10-ketones, however, is similar for all ADHs, as demonstrated by the generally higher activities of 2-heptanone when compared with that of 2-decanone.

Interestingly therefore, to summarise, a biocatalyst is found in this new ADH which exhibits modified or even complementary properties in comparison to earlier ADHs, e.g. from R. erythropolis, which were used either directly from the crude extract or partially purified. These significant differences open up new and interesting fields of application and at the same time document the novelty of this new biocatalyst. Thus, the ADHs comprising the earlier ADHs from R. erythropolis, arising from a crude extract or in the partially purified form, have very different properties with regard to their biochemical properties when compared to the "new" ADH which is both a novel and also an improved biocatalyst. In particular, clear advantages can be seen for the preparation of the industrially highly interesting class of substances comprising optically active aromatic alcohols.

Furthermore, nucleic acid sequences according to the invention, which may also be further improved, which code for the polypeptides involved are preferably suitable for the preparation of whole cell catalysts. The preparation of such biocatalysts is described in principle below and is sufficiently well-known to a person skilled in the art.

The invention also provides a whole cell catalyst containing a cloned gene for a NADH-dependent alcohol dehydrogenase and a cloned gene for an enzyme which is suitable for the regeneration of NADH, in particular a formate dehydrogenase or a NAD-regenerating enzyme such as NADH oxidase.

The further preferred whole cell catalyst, on the other hand, is characterised in that the alcohol dehydrogenase is one from R. erythropolis, in particular according to the invention, the one from DSM 43297.

In the event of the presence of a formate dehydrogenase in the whole cell catalyst, this should be the formate dehydrogenase derived from Candida boidinii and in the event of the presence of a NADH oxidase this should be the NADH oxidase derived from Lactobacillus brevis. An organism like one mentioned in DE10155928 is preferably used as the host organism.

The advantage of an organism of this type is the simultaneous expression of both polypeptide systems, wherein only one rec-organism has to be involved in the reaction. In order to match the rates of reaction for expressing the polypeptides, the corresponding coding nucleic acid sequences can be located on different plasmids with different copy numbers and/or different strength promoters for different strength expression of the nucleic acid sequences can be used. In this type of matched enzyme system, an accumulation of an optionally inhibiting intermediate compound advantageously does not occur and the reaction involved can proceed at an optimal overall rate. However, this is very well-known to a person skilled in the art (Gellissen, G.; Piontek, M.; Dahlems, U.; Jenzelewski, V.; Gavagan, J. W.; DiCosimo, R.; Anton, D. L.; Janowicz, Z. A. (1996), Recombinant Hansenula polymorpha as a biocatalyst. Coexpression of the spinach glycolate oxidase (GO) and the S. cerevisiae catalase T (CTT1) gene, Appl. Microbiol. Biotechnol. 46, 46-54; Farwick, M.; London, M.; Dohmen, J.; Dahlems, U.; Gellissen, G.; Strasser, A. W.; DE19920712).

In addition to this, the present invention provides, in a next aspect, a coupled enzymatic reaction system having cofactor-dependent enzymatic transformation of an organic compound with a polypeptide according to the invention and enzymatic regeneration of the cofactor.

Enzymatic regeneration of the cofactor should advantageously be performed with the formate dehydrogenase derived from the formate dehydrogenase from Candida boidinii or a NADH oxidase derived from the NADH oxidase from Lactobacillus brevis. The reaction system may be understood to be any vessel in which the reaction according to the invention can be performed, that is reactors of any type (loop reactor, stirred tank, enzyme membrane reactor etc.), or diagnosis kits in any form at all.

When using a formate dehydrogenase, cofactor regeneration is performed using formic acid or its salts as a reducing agent. Alternatively, however, other enzymatic or substrate-based cofactor regenerating systems can also be used.

A final use of the alcohol dehydrogenase according to the invention or of the whole cell catalyst according to the invention relates to its use in a process for the asymmetric reduction of ketones. Aqueous buffered solutions are suitable for conversion of the ketones.

The reactions are performed in the pH range which is typical for enzymatic reactions, wherein pH values of between 4 and 9, in particular between 5.5 and 7.5 have proven to be particularly suitable.

The reaction temperatures for the reductive conversions are preferably in the range between 15 and 65° C., in particular between 20 and 40° C.

The nucleic acid sequences according to the invention can thus advantageously be used to prepare rec-polypeptides. Using recombinant techniques which are well-known to a person skilled in the art, organisms are obtained which are capable of providing the polypeptide involved in amounts which are sufficient for an industrial process. The rec-polypeptides according to the invention are prepared using genetic engineering processes which are well-known to a person skilled in the art (Sambrook, J.; Fritsch, E. F. and Maniatis, T. (1989), Molecular cloning: a laboratory manual, $2^{nd}$ ed., Cold Spring Harbor Laboratory Press, New York; Balbas, P. and Bolivar, F. (1990), Design and construction of expression plasmid vectors in E. coli, Methods Enzymol. 185, 14-37; Rodriguez, R. L. and Denhardt, D. T (eds) (1988), Vectors: a survey of molecular cloning vectors and their uses, 205-225, Butterworth, Stoneham). With regard to the general procedures (PCR, cloning, expression etc.) reference is also made to the following literature and the references cited therein: Universal GenomeWalker™ Kit User Manual, Clontech, 3/2000 and the literature cited therein; Triglia T.; Peterson, M. G. and Kemp, D. J. (1988), A procedure for in vitro amplification of DNA segments that lie outside the boundaries of known sequences, Nucleic Acids Res. 16, 8186; Sambrook, J.; Fritsch, E. F. and Maniatis, T. (1989), Molecular cloning: a laboratory manual, $2^{nd}$ ed., Cold Spring Harbor Laboratory Press, New York; Rodriguez, R. L. and Denhardt, D. T (eds) (1988), Vectors: a survey of molecular cloning vectors and their uses, Butterworth, Stoneham.

For application, the polypeptide involved can be used in the free form as homogeneous purified compounds or as a recombinant prepared enzyme. Furthermore, the polypeptide can also be used as a constituent of an intact guest organism or in combination with the digested and any highly purified cell material at all from the host organism. It is also possible to use the enzymes in immobilised form (Sharma B. P.; Bailey L. F. and Messing R. A. (1982), Immobilisierte Biomaterialien—Techniken und Anwendungen, Angew. Chem. 94, 836-852). Advantageously, immobilisation is achieved by lyophilisation (Paradkar, V. M.; Dordick, J. S. (1994), Aqueous-Like Activity of α-Chymotrypsin Dissolved in Nearly Anhydrous Organic Solvents, J. Am. Chem. Soc. 116, 5009-5010; Mori, T.; Okahata, Y. (1997), A variety of lipi-coated glycoside hydrolases as effective glycosyl transfer catalysts in homogeneous organic solvents, Tetrahedron Lett. 38, 1971-1974; Otamiri, M.; Adlercreutz, P.; Matthiasson, B. (1992), Complex formation between chymotrypsin and ethyl cellulose as a means to solubilize the enzyme in active form in toluene, Biocatalysis 6, 291-305). Lyophilisation in the presence of surface-active substances such as Aerosol OT or polyvinylpyrrolidone or polyethylene glycol (PEG) or Brij 52 (diethylene glycol mono-cetyl ether) (Kamiya, N.; Okazaki, S.-Y.; Goto, M. (1997), Surfactant-horseradish peroxidase complex catalytically active in anhydrous benzene, Biotechnol. Tech. 11, 375-378) is very particularly preferred. Immobilisation on Eupergit®, in particular Eupergit C® and Eupergit 250L® (Röhm) is extremely preferred (for a review, see: E. Katchalski-Katzir, D. M. Kraemer, *J. Mol. Catal. B: Enzym.* 2000, 10, 157). Similarly preferred is immobilisation on Ni-NTA in combination with the polypeptide modified by attaching a His-Tag (hexa-histidin) (Petty, K. J. (1996), Metal-chelate affinity chromatography In: Ausubel, F. M. et al. eds. *Current Protocols in Molecular Biology, Vol.* 2, New York: John Wiley and Sons). Use as CLECs is also a possibility (St. Clair, N.; Wang, Y.-F.; Margolin, A. L. (2000), Cofactor-bound cross-linked enzyme crystals (CLEC) of alcohol dehydrogenase, Angew. Chem. Int. Ed. 39, 380-383). By means of these measures, it is possible to generate, from polypeptides which are unstable in organic solvents, those which can operate in mixtures of aqueous and organic solvents or entirely in organic media.

In a final development, the present invention provides use of the vectors prepared from "high copy number" vectors (A) and "moderate copy number" vectors (B) to prepare recombinant proteins tending to form inclusion bodies, wherein at least the replication origin is taken from vector (B) and at least the cloning and expression elements are taken from vector (A).

pET11a is preferably used as vector (A) and pACYC184 is preferably used as vector (B). Vector pAK1 is a prototype of such structures. This vector is composed, as mentioned above, of a segment of the "high copy number" vector pET11a from the Novogen Co. with replication origin ColE1 and the "moderate copy number" vector pACYC184 with replication origin p15A. pET11a contains the ampicillin (AMP) gene as a selection marker, pACYC184 contains two selection markers, chloramphenicol (CAM) and tetracyclin (TET). As a result of ligation of the pET11a fragment in pACYC184, in addition to the selection markers, the T7 promoter thereof, lacI gene and MCS (Multiple Cloning Site; Polylinker) are also introduced into pACYC184.

When using the vector pKA1 prepared according to the invention for the recombinant preparation of ADH according to the invention from *E. coli*, an ADH activity of about 70 U/mg is obtained in the crude extract, whereas only about 6 U/mg activity and a high proportion of insoluble inclusion bodies are obtained with the "high copy number" plasmid pKK223-3 from Amersham.

To prepare native polypeptides according to the invention, harvested cells of *R. erythropolis* are broken down by milling in a glass bead mill and the solid constituents are separated by centrifuging. After purifying the cell-free supernatant liquid from centrifuging using anion exchange chromatography and on phenylsepharose, during which process the activity of the fractions is continuously tested, a polypeptide fraction is obtained which enables amino acid sequence analysis. The start sequence determined and the conservative motives obtained by comparison with known ADHs are used to construct degenerated primers (Seq. 3 und 4), with the aid of which a 500 bp length fragment can be obtained by PCR. Using this fragment, a gene probe (Seq. 13) is prepared with the homologous primers (Seq. 5 and 6).

Nucleotide sequence of the probe (Seq. 13)
ATCCAGTACACGAGAATCGGCGCGGAACCCGAACTCACGGAGATTCCCAA

ACCCGAGCCCGGTCCAGGTGAAGTGCTCCTGGAAGTCACCGCTGCCGGCG

TCTGCCACTCGGACGACTTCATCATGAGCCTGCCCGAAGAGCAGTACACC

TACGGCCTTCCGCTCACGCTCGGCCACGAAGGCGCAGGCAAGGTCGCCGC

CGTCGGCGAGGGTGTCGAAGGTCTCGACATCGGAACCAATGTCGTCGTCT

ACGGGCCTTGGGGTTGTGGCAACTGTTGGCACTGCTCACAAGGACTCGAG

AACTATTGCTCTCGCGCCCAAGAACTCGGAATCAATCCTCCCGGTCTCGG

TGCACCCGGCGCGTTGGCCGAGTTCATGATCGTCGATTCTCCTCGCCACC

TTGTCCCGATCGGTGACCTCGACCCGGTCAAGACGGTGCCGCTGACCGAC

GCCGGTCTGACGCCGTATCACGCGATCAAGCGTTCTCTGCCGAAACTTCG

CGGAGGCTCG

Genomic DNA from *R. erythropolis* is then cleaved with EcoRI and hybridised with the probe, after separating the fragments using gel electrophoresis and blots. Detection of hybridisation is performed via a very specific signal at 5.2 kb. This indicates that the gene being sought is located on a 5.2 kb length EcoRI.

In order to obtain the complete gene sequence, genomic DNA from *R. erythropolis* was again digested with EcoRI, DNA fragments with a length between 5 and 6 kb were isolated and cloned in the pUC18 cloning vector. The plasmid pRE-ADH produced was transformed in *E. coli* XL1 Blue and the clones were screened by PCR with the aid of homologous primers.

The entire sequence of the gene for the ADH can then be determined with the aid of homologous primers.

The native polypeptide from *R. erythropolis* has a tetrameric structure and has a molecular weight of 36.206 kDa per sub-unit. Based on the amino acid sequence, the alcohol dehydrogenase from *R. erythropolis* (RE-ADH) obviously belongs to the group of medium-chain dehydrogenases. The high degree of homology with enzymes in this group and the presence of a typical zinc bonding site ("zinc finger") are points in favour of this. The properties of representatives of this class of dehydrogenases have been defined with respect to ADH from horse liver, this having been investigated the most thoroughly. A number of enzymes with different catalytic properties are now known within this group.

A search in the database "gene library" using the search algorithms BlastNT and EMBL over the internet demonstrated the high homology of RE-ADH with other zinc-containing alcohol dehydrogenases, both long-chain and medium-chain ADHs. The highest homology was produced with a phenylacetaldehyde reductase from *Corynebacterium* sp. ST-10. A comparison of the two genes produced the points of agreement shown in FIG. 3 (SEQ ID NO:1 and SEQ ID NO: 18).

| | Score |
|---|---|
| dbj\|AB020760.2\|AB020760 Corynebacterium sp. ST-10 gene for . . . | 2218 |
| emb\|AL356592.1\|SC9H11 Streptomyces coelicolor cosmid 9H11 . . . | 86 |
| dbj\|AB017438.1\|AB017438 Streptomyces coelicolor orf1, orf2 . . . | 86 |
| emb\|Z11497.1\|BLANSAG B. licheniformis ansA gene for asparagi . . . | 44 |
| gb\|AC006518.17\|AC006518 Homo sapiens 12p13 BAC RPCI11-144O2 . . . | 42 |
| mb\|AL096811.1\|SCI30A Streptomyces coelicolor cosmid I30A . . . | 40 |
| gb\|L15558.1\|TRBRPP0X Trypanosoma cruzi ribosomal protein P0 . . . | 40 |
| gb\|AF263912.1\|AF263912 Streptomyces noursei ATCC 11455 nyst . . . | 38 |
| gb\|AE003796.1\|AE003796 Drosophila melanogaster genomic scaf . . . | 38 |
| gb\|AF170068.1\|AF170068 Streptomyces chibaensis D-xylose iso . . . | 38 |
| gb\|AC006434.5\|AC006434 Genomic sequence for Arabidopsis tha . . . | 38 |
| gb\|U85909.1\|APU85909 Aureobasidium pullulans cosmid pPSR-22 . . . | 38 |
| gb\|U62928.1\|APU62928 Aureobasidium pullulans multidrug resi . . . | 38 |
| emb\|AL021487.1\|CEY45F10B Caenorhabditis elegans cosmid Y45F . . . | 38 |
| emb\|Z97559.1\|MTCY261 Mycobacterium tuberculosis H37Rv compl . . . | 38 |
| gb\|L27467.1\|DROP41A Drosophila melanogaster (cDNA1) protein . . . | 38 |
| emb\|AL049913.1\|MLCB1610 Mycobacterium leprae cosmid B1610 . . . | 38 |
| emb\|X68127.1\|MARIREDM2 M. auratus mRNA for ribonucleotide re . . . | 38 |
| gb\|L27468.1\|DROP41B Drosophila melanogaster (cDNA2) protein . . . | 38 |
| gb\|M21659.1\|ANAATP1 Anabaena sp. (clones lambda-An-700 and . . . | 38 |

The comparison of the gene sequence of alcohol dehydrogenase from R. erythropolis with the highly homologous gene phenyl-acetaldehyde reductase from Corynebacterium sp. ST-10 (FIG. 3, SEQ ID NOS:1 and 18) shows in the upper series the base sequence of RE-ADH, in the lower that of Corynebacterium. Matching bases are labelled with a line. The protein sequences in the two polypeptides agree over 316 amino acids over the entire gene (82%). Agreement is even higher when specific regions are compared. From the N-terminus, there is 100% agreement in the amino acid sequence up to the amino acid which is determined by codon 946-948. After that, starting from the Corynebacterium sequence, there is a deletion in Rhodococcus which leads to a frame shift from this position on and thus to a different amino acid sequence. If the gene sequence is converted into the corresponding amino acid sequence then, starting from the N-terminus, amino acids 1-316 are absolutely identical in the two polypeptides and then, due to the gene frameshift, completely different. In this regard, reference is also made to example 4 in this document.

Transformation and expression of the nucleic acid sequences according to the invention in E. coli is performed by cloning the ADH gene in the vector pKK223-3 from Amersham Pharmacia Biotech. For a better rate of expression, the codon AGA for the amino acid arginine in position 8 was altered to CGT which also codes for arginine. At the same time, a new vector (pKA1—FIG. 1) was generated, and this was transformed in E. coli BL21 (DE3) after ligation of the ADH gene in the vector. In the cell-free crude extract, an activity of 70 U/mg was shown with respect to the conversion of p-Cl-acetophenone. In comparison to that, the activity in the crude extract from R. erythropolis with P-Cl-acetophenone was about 2.5 U/mg.

The advantageous aspects and differences mentioned above with regard to improvement in the stability, as compared with previously known alcohol dehydrogenases from R. erythropolis are summarised in Table 5 and in FIG. 4. For better comparison, the relevant enzyme activity measured at 45° C. was set at 100%.

Here, for the very pure new alcohol hydrogenase, high thermal stabilities were produced over a wide temperature range extending up to 65° C. The stability values in this case are 100 to 105° C. In contrast, a significant temperature sensitivity was observed with the previously known alcohol dehydrogenases from R. erythropolis, with a marked decrease in the temperature range from 45 to 60° C. from a relative activity of 100% to only 38%.

TABLE 5

| Incubation conditions 10 min at | ADH according to (DE 4209022, 1991) | new ADH |
|---|---|---|
| 45° C. | 100% (1.7 U/ml) | 95% (110 U/ml) |
| 50° C. | 91% (1.55 U/ml) | 95% (110 U/ml) |
| 55° C. | 78% (1.33 U/ml) | 99% (115 U/ml) |
| 60° C. | 38% (0.65 U/ml) | 97% (112 U/ml) |
| 65° C. | | 100% (116 U/ml) |

Another noteworthy difference from known alcohol dehydrogenases from R. erythropolis, associated with a considerable improvement in enantioselectivity, is seen by comparing the change in enantioselectivity during a reaction using R. erythropolis cells, the crude extract disclosed in the literature and the new ADH from R. erythropolis.

Our results with whole cells of R. erythropolis indicate that this strain contains several ADHs, including at least one with opposite enantioselectivity. If whole cells which have been immobilised with alginate are reacted continuously with p-chloroacetophenone (1.5 mM; 2 ml per h) in a column (5 cm packed height, 1.2 cm diameter; 5.7 ml packing volume), enantiomerically pure(S)-p-chloro-2-phenylethanol is initially obtained in the discharge at almost complete conversion. However, this high ee value is retained for only about 10 h (about 3 volume changes), then the ee value drops drastically while the conversion remains at the same high level. After 25 h (about 9 volume changes) (S)-p-chloro-2-phenylethanol with 70% ee is obtained and after 50 h (about 18 volume changes) the alcohol exhibits only about 5% ee.

The "new" alcohol dehydrogenase described here converts p-chloroacetophenone completely to the enantiomerically pure form. Even when used several times or at higher concentrations, the formation of (R)-p-chloro-2-phenylethanol is never observed. Thus, the enzyme was used in immobilised form repeatedly 11 times (see example 8), wherein the product was always the enantiomerically pure (S)-alcohol war.

Optically enriched (enantiomerically enriched, enantiomer enriched) compounds in the context of this invention is understood to mean the presence of >50 mol % of one optical antipode mixed with the other.

The expression nucleic acid sequences is intended to include all types of single-strand or double-strand DNA and also RNA or mixtures of the same.

An improvement in activity and/or selectivity and/or stability means, according to the invention, that the polypeptides are more active and/or more selective and are more stable under the reaction conditions used. Whereas the activity and stability of enzymes for industrial application should naturally be as high as possible, with regard to the selectivity an improvement is referred to either when either the substrate selectivity decreases or the enantioselectivity of the enzymes increases. For the expression not substantially reduced, used in this connection, the same definition applies mutatis mutandis.

The claimed protein sequences and nucleic acid sequences also include, according to the invention, those sequences which have a homology (excluding natural degeneration) of greater than 91%, preferably greater than 92%, 93% or 94%, more preferably greater than 95% or 96% and particularly preferably greater than 97%, 98% or 99% to one of these sequences, provided the mode of action or purpose of such a sequence is retained. The expression "homology" (or identity) as used herein can be defined by the equation H (%)=[1−V/X]×100, where H means homology, X is the total number of nucleobases/amino acids in the comparison sequence and V is the number of different nucleobases/amino acids in the sequence being considered with reference to the comparison sequence. This also applies to the part-region of a gene sequence with the bases 1-948 in FIG. 3. In each case the expression nucleic acid sequences which code for polypeptides includes all sequences which appear to be possible, in accordance with degeneration of the genetic code.

The literature references mentioned in this document are regarded as being included within the disclosure.

EXAMPLE 1

Purifying Alcohol Dehydrogenase and Obtaining Partial Sequence Data

*R. erythropolis* was cultivated in medium DSM 65 (per 1 litre: 4 g glucose, 4 g yeast extract, 10 g malt extract; pH 7.2) for 3 days at 30° C. under aerobic conditions. After harvesting the cells, these were resuspended using a buffer (addition of 1.5 ml tris-HCl buffer, pH 7.4 per 1 g of cells) and broken down by milling with glass beads. The solid constituents and cell fragments were removed by centrifuging and the cell-free supernatant liquid was used as the crude extract for further purification.

A first purification can be achieved by anion exchange chromatography (MonoQ-Material, Pharmacia) (mobile buffer: 50 mM TEA buffer, pH 7.0; elution with a NaCl gradient of 0-1 M). A photometric test (measurement at 340 nm) with p-Cl-acetophenone (1.5 mM p-Cl-acetophenone, 0.25 mM NADH 0.1 M Kpi buffer, pH 6.0) showed that the desired enzyme is eluted at about 0.8 M NaCl. The fraction with the highest activity is treated with ammonium sulfate (1.8 M final concentration) and applied to a phenylsepharose CL-4B column (Pharmacia). For elution, a falling ammonium sulfate gradient (1-0 M) was used; the desired enzyme then eluted at almost 0 M ammonium sulfate. Here again the most active fraction is also treated with ammonium sulfate (1 M final concentration) and applied to another column filled with butylsepharose FF. The desired protein eluted on application of a falling ammonium sulfate gradient (1-0 M) at about 0.1 M ammonium sulfate.

The protein material obtained at this stage proved sufficiently clean to be used for amino acid sequence analysis (automated Edman degradation using an Automated Sequencer 4774 (Applied Biosystems) with online HPLC 120 A). The sequence read: MKAIQYTRI.

EXAMPLE 2

Determining the Gene Sequence

Database searches show that enzymes which belong to the group of alcohol dehydrogenases have characteristic conserved regions. These regions are e.g.:

gene sequence 1:

(Seq. 14)

EPELTEIPKPEPGPGEVLLEVTAAGV<u>CHS</u>DDF gene sequence 2:

(Seq. 15)

PLTL<u>GHE</u>GAGKVAAVGEGVEGLDIGT gene sequence 3:

(Seq. 16)

<u>CGNCWHC</u>SQGLENYC gene sequence 4:

(Seq. 17)

HLVPIGDLDPVKTVPLTDAGLTPYHAIKRSLPKLRGGSYAVVI<u>GTGGL</u>.

Sections emphasised by underscoring are motives which can be classified as functional: in sequences 1, 2 and 3 these are motives which are responsible for zinc-bonding ("zinc finger"), in sequence 4 some of the amino acids responsible for binding NAD.

Sequences from these conserved regions can be used, together with the N-terminal sequence, for isolating the gene for alcohol dehydrogenases. For isolating the desired enzyme from *R. erythropolis* degenerated primers from the N-terminal sequence MKAIQYTRI (5'-Primer) and the sequence YAVVIGTG (3'-Primer) obtained from the database information are used.

The following was used as the 5'-primer:

(Seq. 3)

5' ATG AAG GCG(C) ATC CAG TAC ACG(C) CGG(C) ATC 3' and the following as the 3'-primer:

(Seq. 4)

5'- GCC GGT ACC AAT(C) GAC(G) AAC(G) CGC GTA- 3'

A PCR reaction was performed with these primers, by means of which an about 500 bp length fragment could be amplified. Sequence analysis and database searches showed a high degree of homology with phenylacetaldehyde reductase from *Corynebacterium* sp. and with other zinc containing alcohol dehydrogenases (see above).

To isolate the complete gene, a probe was prepared from the 500 bp length fragment and this was used to perform Southern blot hybridisation. In order to guarantee the specificity of the hybridisation reaction, homologous primers from internal sequences of the 500 bp fragment were constructed in order to prepare the probe.

The following were used as homologous primers:

5'-PrimerH:

(Seq. 5)

5'-ATC CAG TAC ACG CGC ATC GGC GCG GAA-3'

-continued

3'-PrimerH:
(Seq. 6)
5'-GCC TCC GCG AAG TTT CGG CAG AGA ACG-3'

By digesting the genomic DNA with different restriction endonucleases, a gene library was compiled and a specific signal at 5.2 kb was obtained by subsequent Southern blot hybridisation. This showed that the gene being looked for is located on a 5.2 kb length EcoRI fragment.

Using specific primers, derived from the cleavage sites of restriction enzymes and sequences from the 500 bp fragment, further fragments are then obtained by means of PCR, wherein, with the aid of overlapping DNA sequences and the stop codon, the entire sequence can be defined.

From the primary structure, the molecular weight of RE-ADH can be determined, this being 36.206 kD. Since a molecular weight of about 150,000 was determined using gel filtration (Superdex G-200, Pharmacia), RE-ADH in the native form is an enzyme with a tetrameric structure.

EXAMPLE 3

Cloning and Heterologous Expression of RE-ADH a) Cloning the RE-ADH Gene (Wild Type) in Vector pKK223-3

For expression of the RE-ADH gene, the plasmid pKK223-3 was first selected (Amersham Pharmacia Biotech).

The ADH gene was amplified using PCR under the following conditions:

For denaturation of the DNA, this was incubated for 3 min at 94° C. This was then followed by 30 cycles consisting of:

| Denaturation: | 45 sec; 94° C. |
|---|---|
| Annealing: | 30 sec; 64° C. |
| Extension: | 110 sec; 68° C. |
| Concluding step: | 10 min.; 68° C. |
| Cooling: | 6° C. |

The reaction volume was 50 µl.

AdvanTaq DNA polymerase (CLONTECH) was used as polymerase for the reaction.

Since the genomic DNA from *R. erythropolis* GC was rich (63%), 5% of DMSO was added to the mixture in order to increase the efficiency of the PCR reaction. The following oligonucleotide primers with restriction cleavage sites for the restriction endonucleases EcoRI and HindIII were used (Metabion):

5'- Primer:
(Seq. 7)
5'-GCG GAA TTC ATG AAG GCA ATC CAG TAC ACG-3'

3'- Primer:
(Seq. 8)
5'-CGC AAG CTT CTA CAG ACC AGG GAC CAC AAC-3'

To clone the gene, the PCR product and the plasmid DNA vector pKK223-3 (1-2 µg) were digested with the restriction endonucleases EcoRI and HindIII (10 U) (37° C., 2 h). The endonucleases were inactivated at the end of the reaction by heating at 65° C. for 20 min.

The restriction mixtures were separated by molecular weight on agarose gel and the DNA isolated from the gel (QIAquick Gel Extraction Kits, Qiagen). The vector pKK223-3 was dephosphorylated (6 U shrimp alkaline phosphatase), in order to avoid religation of the linearised vector DNA. This reaction was performed at 37° C. for 1 hour, the enzyme was then inactivated by heating at 65° C. for 15 min.

The PCR product (insert) was ligated with the vector (equimolar quantities). The ligation mixture contained 5 U $T_4$ ligase and ligation was performed at 25° C.

To express the RE-ADH gene, the plasmid pRE-ADH 1 which was produced was transformed in competent *E. coli* JM 105 cells. The growth of recombinant *E. coli* cells took place on agar plates with $LB_{amp}$ medium (LB medium with ampicillin 100 µg/ml as selection marker) at 37° C. for 16 h.

Colonies on the agar plates were cultivated in 5 ml $LB_{amp}$ liquid medium for 16 h at 30° C. for expression. This culture was used as the preculture for a main culture (1:100 inoculated). Gene expression was induced at an optical density ($OD_{600\ nm}$) of 0.3 by adding 1 mM IPTG, the induced cells then continued to grow for another 16 h at 30° C. on a cylindrical shaker (120 rpm).

For the activity test, the cells were harvested (15 min centrifuging at 14000 rpm, 4° C.) and degraded after resuspension with 100 mM KPi buffer, pH 6.0 (1.5 ml of buffer per 1 g of cells). For the purposes of degradation, the suspension was treated with ultrasound (2×30 sec. power 100%, pulse 50), then the cell broth was centrifuged. The supernatant liquid is the soluble crude extract, the sediment is the insoluble fraction. Both fractions were tested photometrically for activity of the alcohol dehydrogenase (standard test with p-Cl-acetophenone and NADH). In the soluble fraction, a specific enzyme activity of 6 U/mg was measured (1 U=decrease of 1 µMol NADH per minute).

b) Cloning the RE-ADH Gene (Mutants) in Vector pKA1

In order to achieve a better rate of expression in *E. coli*, a mutation was introduced with which the codon AGA coding for the amino acid arginine in position 8 in the codon was altered to CGT also coding for arginine (Replacement of "minor codons" (Chen, G. T., Inouye, M., Nucleic Acids Res. Vol. 18 (1990), 1465; Chen, G. T., Inouye, M., Genes Dev. Vol. 8 (1994), 2641).

-Production of Mutants with a Modified Codon:

The gene was amplified using PCR, wherein the following PCR conditions were used:

To denature the DNA, this was incubated for 3 min at 94° C. This was then followed by 30 cycles consisting of:

| Denaturation: | 45 sec; 94° C. |
|---|---|
| Annealing: | 30 sec; 64° C. |
| Extension: | 110 sec; 68° C. |
| Concluding step: | 10 min.; 68° C |
| Cooling: | 6° C. |

The reaction volume was 50 µl.

AdvanTaq DNA polymerase (CLONTECH) was used as polymerase for the reaction. The following nucleotide primers with the restriction cleavage sites NdeI and BamHI were used:

5'-Primer
(Seq. 9)
5' -GAG GTC GGT CAT ATG AAG GCA ATC CAG TAC ACG <u>CGT</u> ATC GGC- 3'

-continued

The 5'-Primer contains the replacement of AGA by CGT

3'-Primer
(Seq. 10)
5'- CGC GGA TCC CTA CAG ACC AGG GAC CAC AAC - 3'

-Construction of the Pasmid pKA1

This plasmid was constructed from the plasmid vector pET11a, replication origin ColE1 (Novagen) and the moderate copy number plasmid vector pACYC184, replication origin p15A (Biolabs). pET11a contains the ampicillin (Amp)-resistant gene as a selection marker, pACYC184 contains two selection markers, the genes for chloramphenicol (Cam)-resistance and tetracyclin (Tet)-resistance.

The plasmid pET11a was digested with the restriction nucleases HindIII and NruI. the 2500 bp length fragment contained the expression elements lac I, T 7 promoter, T 7 terminator. This fragment was ligated in plasmid pACYC184 via the cleavage sites HindIII and NruI. In this case the plasmid pACYC184 was cleaved with the two restriction endonucleases HindIII and NruI. This inactivated the tetracyclin-resistance gene (Tet). The plasmid pKA1 (5559 bp length) which was produced was transformed in $E.$ $coli$ XL1 Blue and plated out on LB agar plates with chloramphenicol, 40 µg/ml.

In order to check the length of the plasmid experimentally, two colonies were picked out from the $LB_{cam}$ agar plates and cultivated for 16 h in 5 ml $LB_{cam}$. The plasmids were isolated and used for restriction analysis: the plasmids were cleaved with EcoRI and the length determined on an agarose gel (0.8%). A length of 5559 bp was determined in this way. This plasmid was used to clone and express the RE-ADH.

For cloning and expression of RE-Adh in the pKA1 vector, the gene fragment containing the mutation (see above) and vector pKA1 were digested with the restriction endonucleases NdeI and BamHI, the fragments were applied to agarose gel 0.8% and purified from the gel (QlAquick Gel Extraction Kits, Qiagen). Vector and insert were ligated (equimolar quantities). Ligation was performed at 25° C. with 5 U $T_4$ ligase. The construct pRE-ADH4 was first transformed in $E.$ $coli$ XL1 Blue cells and incubated on $LB_{cam}$ agar plates for 16 h at 37° C. The success of cloning was checked using restriction analysis. Here five colonies were picked out from the agar plates and the plasmids were isolated (QIAprep Spin Miniprep Kit, Qiagen) and sequenced.

For expression, $E.$ $coli$ BL21 (DE3) was used as host. Recombinant cells were multiplied in the medium $LB_{cam}$ at 37° C. At an $OD_{600}$ of 0.5, expression was induced with 25 µM IPTG, then the cells were multiplied for 12 h at at 30° C. The cells were harvested after centrifuging for 15 min at 5000 rpm, the sediment was resuspended in 100 mM Kpi buffer (1.5 ml per 1 g of cells) and broken down using ultrasound. The cell-free crude extract exhibited an enzyme activity of 70 U/mg (measured with p-Cl-acetophenone and NADH).

EXAMPLE 4

Biochemical Comparison of Alcohol Dehydrogenase from R. erythropolis with Aldehyde Reductase from Corynebacterium sp When comparing the gene sequence for ADH from R. erythropolis with sequences in the databases, it was shown that RE-ADH has a high degree of homology with an aldehyde reductase from Coyrnebacterium sp. In the publication on aldehyde reductase, a number of biochemical properties of this enzyme are described (Itoh, N., R. Morihama, J. Wang, K. Okada and N. Mizuguchi (1997), Purification and characterisation of phenylacetaldehyde reductase from a styrene-assimilating Corynebacterium strain, ST-10, Appl. Environ. Microbiol. 63: 3783-378). Some of the (aldehyde) substrates described in that publication were therefore also converted using RE-ADH and compared using the relative activities of the reductase. Table 6 summarises these results with aldehydes, in addition the activities of the two enzymes with respect to reaction with acetophenone are also given. Further comparisons of the two enzymes using the published data material are not meaningful because the enzyme from Corynebacterium was tested exclusively with phenylacetaldehyde as substrate, but RE-ADH has hitherto been characterised using p-Cl-acetophenone.

Table 6:

A comparison of RE-ADH with the aldehyde reductase from Corynebacterium sp. with regard to the activity for acetophenone reduction and and a few aldehydes. Data on the enzyme from Corynebacterium were taken from the publication by Itoh et al. (see above), data on RE-ADH are our own measurements (homogeneous=very pure homogeneous enzyme). For a comparison using relative activities, the activity of the two enzymes was given with respect to phenylacetaldehyde=100%.

| Substrate | Corynebacterium | Rhodococcus |
|---|---|---|
| Acetophenones | 22.4 U/mg (homogeneous) | 348 U/mg (homogeneous) |
| Phenylacetaldehyde | 100 | 100 |
| p-Cl-acetophenone | 338 | 288 |
| Acetophenone | 35 | 87 |
| Valeraldehyde | 181 | 433 |
| Caprylic aldehyde | 1220 | 522 |

The results show that the C-terminal sequence differences in the two enzymes also result in different biochemical properties. The activities of the two highly purified enzymes differ considerably; Rhodococcus ADH is about 15 times more active towards acetophenone than the Corynebacterium enzyme. The relative substrate spectrum also exhibits differences: the high activity of the Corynebacterium enzyme towards caprylic aldehyde (12 times that with respect to acetophenone) does not occur with the RE-ADH enzyme, here the activity towards caprylic aldehyde is only about 5 times that towards acetophenone. Also, the ratio p-Cl-acetophenone/acetophenone is different: for Corynebacterium it is about 10:1, but for RE-ADH it is 3:1.

These examples show that the two enzymes differ significantly from each other and these differences are attributed to the sequence differences in the C-terminal region.

EXAMPLE 5

Biochemical Characterisation of Alcohol Dehydrogenase from R. erythropolis a) Substrate Spectrum Table 7: Substrate specificity of the new ADH from R. erythropolis for ketones and ketoesters.

Table 7 given below shows that the alcohol dehydrogenase from *R. erythropolis* accepts a number of ketones and ketoesters and thus is suitable for the preparation of aromatic and aliphatic secondary alcohols. In this case, the relative activity is given with respect to the activity measured for acetophenone.

| Substrate | Relative activity [%] |
|---|---|
| Ketones | |
| Acetophenone | 100 |
| p-Cl-acetophenone | 1198 |
| m-Cl-acetophenone | 2384 |
| p-F-acetophenone | 194 |
| p-methyl-acetophenone | 640 |
| p-methoxy-acetophenone | 232 |
| Phenoxyacetone | 4180 |
| Heptan-2-one | 3328 |
| Decan-2-one | 2521 |
| Oxo esters | |
| Methyl acetoacetate | 134 |
| Ethyl acetoacetate | 1020 | b) Km Values

For the reduction reaction, RE-ADH exhibits a Km value of 0.5 mM for the substrate p-Cl-acetophenone and for the coenzyme NADH of 0.025 mM. For the oxidation reaction, the value for (S)-p-Cl-phenylethanol is 0.28 mM and the value for NAD is 0.082 mM.

c) pH Optimum for the Activity and Stability

The pH optimum for RE-ADH is at pH 6.0 for the reduction reaction (measured using p-Cl-acetophenone).

On storing the enzyme at 4° C. and room temperature for 1 and 2 days, there is no deactivation in the range 7.5-8.5 (tris-HCl buffer, 0.1 M).

EXAMPLE 6

Preparative Applications of ADH from *R. erythropolis*

The preparative potential of the enzyme will be indicated by reacting a few keto-compounds.

a) Reduction Reactions

Reduction has to be coupled with a regeneration reaction for the coenzyme NADH, for example the reaction with formate dehydrogenase and formate. However, all other NADH-producing reactions may also be used. The product is analysed by means of gas chromatography, wherein the stationary phase in the GC column is capable of separating enantiomeric alcohols so that information on the ee values of the enzymatically prepared product can be obtained.

Such a mixture for reduction contains:
10 mM keto-compound
0.5 mM NAD
100 mM Na formate
1 U/ml formate dehydrogenase
0.5 U/ml of alcohol dehydrogenase (partially purified by means of ion exchange chromatography; units are photometrically measured in the standard test using p-Cl-acetophenone and NADH)

At the times 0, 5 min and 10 min, samples are taken (100 µl), extracted with 100 µl of chloroform and the chloroform phase is analysed using gas chromatography.

GC Analysis:

Column: CP-Chirasil-DEX CB length: 25 m, diameter: 25 µm (Chrompack). Temperature programme: 5 min at 60° C., then 5° C./min up to 190° C. (for hexanone/hexanol: 30 min at 60° C., then 10° C./min to 195° C.). Column flow 1.3 ml/min; gas:helium The Following were Used as Keto-Compounds:

p-Cl-acetophenone, acetophenone, ethyl 2-oxobutyrate, 2-hexanone and 2-heptanone. Table 8 summarises the data on product purity. All the compounds were fully converted after 10 min; analysis by gas chromatography showed that only one enantiomer was formed with each reactant. The enzyme thus reduced keto-compounds in a highly enantioselective manner.

TABLE 8

Proof of enantiomer purity of the products formed by enzymatic reduction

| Substrate (retention time) | Retention time of product | Conversion after 10 min [%] | ee [%] of the product |
|---|---|---|---|
| Acetophenone (16.9 min) | 21.2 min | >95% | >99% |
| 4-Cl-acetophenone (21.8 min) | 24.2 min | >95% | >99% |
| Ethyl 2-oxobutyrate (10.4 min) | 14.1 min | >95% | >99% |
| 2-hexanone | 22.4 min | >95% | >99% |
| 2-heptanone | 15.2 min | >95% | >99% | b) Oxidation Reactions

By means of enantioselective oxidation of an alcohol, an enantiomer-enriched or enantiomer-pure alcohol, for example, can be obtained from a racemate. By way of example, this has been demonstrated for the production of (R)-phenylethanol:

The following were used: 10 mM (R,S)-phenylethanol, 0.5 mM NADH, 50 mM tris-HCl buffer pH 7.5 with 2 mM DTT, 1 U ADH from *R. erythropolis* and 2 U NADH oxidase (from *Lactobacillus brevis* DSM 20054 in accordance with (DE10140088).

Samples were taken after 0, 1 and 2 h and separated by gas chromatography (column: CP-Chirasil-DEX CB length: 25 m, diameter: 25 µm (Chrompack). Temperature programme: 5 min at 60° C., then 5° C./min up to 190° C.; column flow rate 1.3 ml/min; gas: helium. In this case, both the acetophenone peak (product; retention time=16.9 min), and also the enantiomers of phenylethanol (reactants; retention times R-phenylethanol=20.8 min and S-phenylethanol=21.1 min) were recorded.

Analysis showed that (S)-phenylethanol was fully oxidised after 2 h and a corresponding amount of the oxidation product acetophenone could be found by gas chromatography. (R)-phenylethanol remained untouched so an ee value of >99% is obtained for this enantiomer.

EXAMPLE 7

Immobilising the Enzyme

RE-ADH can be immobilised using a variety of coupling methods and support materials. For example the enzyme can be bonded to support materials such as Eupergit® via a covalent bond.

a) Immobilising on Eupergit® (Trade Name; Röhm/Degussa)

Eupergit C® and Eupergit C 250L® were used in parallel batches, each being loaded with partially purified RE-ADH (literature reference relating to Eupergit immobilisation: E. Katchalski-Katzir, D. M. Kraemer, *J. Mol. Catal. B: Enzym.* 2000, 10, 157). The following was used for the test:

1.5 mM p-Cl-acetophenone (dissolved in 0.1 M Na formate buffer, 0.05 M KPi buffer, pH 6.0)
0.5 mM NAD
30 mg immobilisate
1 U/ml formate dehydrogenase (FDH)

These test materials were incubated at 30° C., a sample (100 µl) was taken from each mix after 0, 5, 10 and 15 min, this was extracted with 100 µl of chloroform and the chloroform phase was analysed for any phenylethanol formed using gas chromatography. The activity of the immobilised enzyme can be calculated from the kinetics of phenylethanol formation and values of 11.8 U/g support for Eupergit C® and 8 U/g of support for Eupergit C 250L® were obtained. With respect to the amount of enzyme used, this corresponded to coupling yields of 1% (Eupergit ®) and 0.8% (Eupergit C 250L®).

b) Immobilising on Ni-NTA

For immobilisation on Ni-NTA, the enzyme was provided with a His-Tag (hexa-histidine) at the C-terminus, using genetic engineering techniques.

-Modifying the RE-ADH Gene:

The following nucleotide primers were constructed in order to produce a hexa-histidine group at the C-terminus:

```
5'-Primer:
                                          (Seq. 11)
5'- GGT GAA TTC ATG AAG GCA ATC CAG TAC ACG CGT

ATC GGC -3'
```

A silent mutation for the amino acid in position 8 (replacement of the arginine codon AGA by CGT) via the 5'-Primer.

```
3'-Primer:
                                          (Seq. 12)
5'- CGC AAG CTT CTA GTG GTG GTG GTG GTG GTG CAG

ACC AGG GAC- 3'
```

This primer, with 6 codons for histidine, facilitates the introduction of 6 histidine groups at the C-terminus of RE-ADH.

The gene was amplified with these primers using PCR under the conditions described previously.

The pKK223-3 plasmid vector and the PCR product were digested with EcoRI and HindIII. After ligation of the two fragments (reaction at 25° C. with 5 U $T_4$ ligase), the plasmid pRE-ADH5 produced was first transformed in *E. coli* XL1 Blue and incubated with $LB_{amp}$ medium for 16 h at 37° C. on agar plates. The success of cloning can be monitored using restriction analysis. For expression, the vector pRE-ADH5 was transformed in *E. coli* JM105 and cultivated for 16 h in $LB_{amp}$ medium at 37° C. On achieving an $OD_{600}$ of 0.5, gene expression was induced by adding 1 mM IPTG. After a further 12 hours of growth, the cells could be harvested and the activity of the RE-ADH tested.

An enzyme activity of 7 U/mg was measured. This activity value showed that modification of the gene by linking a hexa-histidine group to the C-terminus had no effect on the enzyme activity.

-Performing Immobilisation:

Recombinant *E. coli* JM105/pRE-ADH5 cells were broken down in an imidazole-containing buffer (50 mM $NaH_2PO_4$; 300 mM NaCl; 10 mM imidazole, pH 8.0) and a crude extract was prepared in the way described previously. For immobilisation, 1 ml of enzyme solution (13 U/ml RE-ADH, crude extract from the culture *E. coli* JM105pRE-ADH5; 8 mg/ml of protein) was added to 300 mg of Ni-NTA support material (Quiagen) and incubated for 10 min at 0° C. (ice bath). After centrifuging the suspension, 3 U/ml could still be detected as residual activity in the supernatant liquid as non-bonded enzyme. The immobilisate was reacted with p-Cl-acetophenone to detect the bonded activity.

Figure 2:
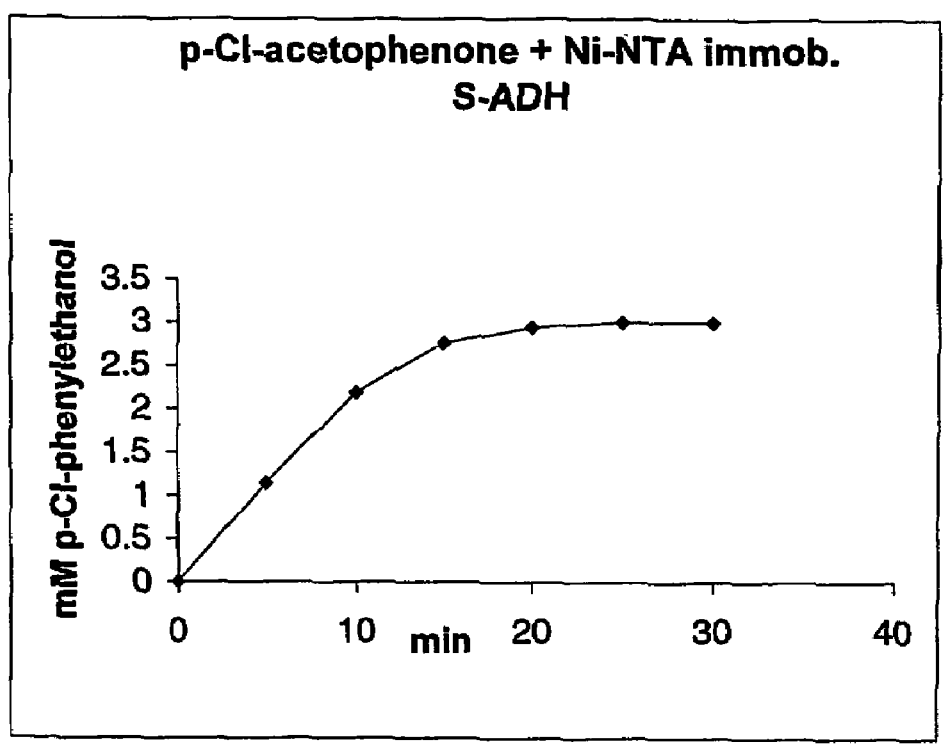

For this purpose, the following were used per 1 ml of total volume:

30 mg immobilisate
3 mM p-Cl-acetophenone (substrate; dissolved in 100 mM Na formate, 50 mM Kpi buffer pH 6.0)
0.5 mM NAD
1 U formate dehydrogenase The test batch was incubated in the same way as described above (immobilisation on Eupergit®), samples were taken and these were analysed using gas chromatography. FIG. 2 shows the kinetics of the reaction; based on the kinetics of formation of p-Cl-phenylethanol, an activity of 0.21 U can be calculated therefrom. Taking into account the fact that this test was performed with 30 mg of immobilisate and that 10 U RE-ADH had bonded to 300 mg of support material, 1 U was thus introduced in the test batch with the 30 mg. Since an activity of 0.21 U was reported, an immobilisation yield of 21% was obtained. The enantiomer purity (ee value) of the alcohol formed with the immobilisate was >99%.

The invention claimed is:

1. An isolated cell comprising a cloned polynucleotide comprising SEQ ID NO:1 or a polynucleotide that hybridizes under stringent conditions to the full length complement of SEQ ID NO:1 and which encoding an NADH-dependent alcohol dehydrogenase, wherein the stringent conditions comprise washing in 1×SSC and 0.1% SDS for 1 hour at 50° C., and 0.2×SSC and 0.1% SDS at 68° C. for 1 hour and a cloned polynucleotide for a *Candida boidinii* formate dehydrogenase or *Lactobacillus brevis* NADH oxidase.

2. The cell according to claim 1, comprising SEQ ID NO:1.

3. The cell according to claim 1, which comprises *Candida boidinii* formate dehydrogenase and *Lactobacillus brevis* NADH oxidase.

* * * * *